(12) United States Patent
Alphandary et al.

(10) Patent No.: US 8,828,286 B2
(45) Date of Patent: Sep. 9, 2014

(54) DENTAL RESTORATION CONDITIONING APPARATUS AND METHOD

(75) Inventors: Adi Alphandary, Hod Hasharon (IL); Moises Fleitman, Herzeliya (IL); Nitzan Bichacho, Tel Aviv (IL); Yuval Jacobi, Tel Aviv (IL)

(73) Assignee: Naym 55 Dental Technologies Ltd., Hod Hasharon (IL)

( * ) Notice: Subject to any disclaimer, the term of this patent is extended or adjusted under 35 U.S.C. 154(b) by 558 days.

(21) Appl. No.: 13/022,214

(22) Filed: Feb. 7, 2011

(65) Prior Publication Data

US 2011/0129790 A1 Jun. 2, 2011

Related U.S. Application Data

(63) Continuation-in-part of application No. PCT/IL2009/000769, filed on Aug. 6, 2009.

(60) Provisional application No. 61/136,012, filed on Aug. 6, 2008.

(51) Int. Cl.
*A61C 13/14* (2006.01)
*B29C 35/08* (2006.01)
*A61C 13/15* (2006.01)
*A61C 19/00* (2006.01)

(52) U.S. Cl.
CPC ............. *A61C 19/002* (2013.01); *A61C 19/003* (2013.01); *Y10S 425/011* (2013.01)
USPC .............. 264/16; 264/17; 425/85; 425/174.4; 425/DIG. 11

(58) Field of Classification Search
USPC ....... 425/173, 174.4, DIG. 11; 433/29, 203.1; 264/494, 16, 17, 19
See application file for complete search history.

(56) References Cited

U.S. PATENT DOCUMENTS

RE7,272 E * 8/1876 McDermut ..................... 264/16
2,368,816 A * 2/1945 Felcher ........................ 425/175
2,392,929 A * 1/1946 Lee ................................ 264/19

(Continued)

FOREIGN PATENT DOCUMENTS

CH 599 812 A5 5/1978
CH 000599812 A * 5/1978 ............... B08B 3/04

(Continued)

OTHER PUBLICATIONS

Porcelain Veneers: Bonding Procedures, USCSD Procelain Veneer Restoration, four pages, found on-line at http://www.usc.edu/hsc/dental/rest/tooth_restorations/INSERTION_OF_PV_REST.pdf, (2001).

(Continued)

*Primary Examiner* — Yogendra Gupta
*Assistant Examiner* — Emmanuel S Luk
(74) *Attorney, Agent, or Firm* — Vorys, Sater, Seymour and Pease LLP; Susanne M. Hopkins; William L. Klima

(57) ABSTRACT

Provided is a dental restoration conditioning apparatus including a housing formed with a liquid-tight dental restoration treating space including a liquid drain. The housing is configured with a disposable dental restoration grip including at least one resilient vacuum cup, each of the at least one vacuum cup being in fluid communication with at least one vacuum source.

24 Claims, 21 Drawing Sheets

(56) References Cited

U.S. PATENT DOCUMENTS

| | | | |
|---|---|---|---|
| 2,799,054 A * | 7/1957 | Van Rossem | 264/225 |
| 3,664,786 A * | 5/1972 | Devine | 425/99 |
| 3,682,571 A * | 8/1972 | Greenberg et al. | 425/193 |
| 3,682,580 A * | 8/1972 | Greenberg et al. | 425/174.4 |
| 3,974,539 A | 8/1976 | Barouh et al. | |
| 4,073,530 A | 2/1978 | Seidler | |
| 4,479,672 A | 10/1984 | Jermyn | |
| 4,655,700 A * | 4/1987 | Ahmed | 425/73 |
| 4,822,278 A | 4/1989 | Oliva et al. | |
| 4,834,654 A | 5/1989 | Nussbaum | |
| 4,944,901 A * | 7/1990 | Kwok | 264/19 |
| 4,953,902 A | 9/1990 | Brown | |
| 4,993,949 A | 2/1991 | Hill | |
| 5,040,981 A | 8/1991 | Oliva | |
| 5,135,685 A * | 8/1992 | Masuhara et al. | 264/406 |
| 5,135,686 A * | 8/1992 | Masuhara et al. | 264/406 |
| 6,182,820 B1 | 2/2001 | Rathbauer | |
| 6,843,967 B2 * | 1/2005 | Clark | 422/186 |
| 7,090,073 B2 | 8/2006 | Barnes | |
| 7,950,131 B2 * | 5/2011 | Hilliard | 29/564 |
| 7,997,886 B2 * | 8/2011 | Kuo | 425/174.4 |
| 2003/0193119 A1 * | 10/2003 | Zychek et al. | 264/494 |
| 2004/0265771 A1 | 12/2004 | DiMarino et al. | |
| 2007/0065769 A1 * | 3/2007 | Rohner et al. | 433/29 |
| 2007/0104609 A1 | 5/2007 | Powell | |
| 2007/0141530 A1 | 6/2007 | Graham | |
| 2008/0093758 A1 * | 4/2008 | Wachter et al. | 264/16 |
| 2008/0267817 A1 | 10/2008 | Coyle | |

FOREIGN PATENT DOCUMENTS

| | | | |
|---|---|---|---|
| DE | 32 14 764 A1 | 10/1983 | |
| DE | 003934928 A1 * | 10/1989 | A61C 17/02 |
| DE | 39 34 928 A1 | 4/1991 | |
| EP | 0 679 406 A1 | 11/1995 | |
| EP | 1 486 181 A1 | 12/2004 | |
| KR | 2000-0053033 A | 8/2000 | |
| KR | 2002-0057094 A | 7/2002 | |
| TW | 400226 B | 11/1986 | |
| WO | 95/26692 A1 | 10/1995 | |
| WO | 2006/033482 A1 | 3/2006 | |

OTHER PUBLICATIONS

Magne, et al., "Bonded Porcelain Restorations in the Anterior Dentition: A Biomimetic Approach", Chapter 8, pp. 335-352, Chicago: Quintessence Publishing Co.; (2002).

Gürel, et al., "Atlas of Porcelain Laminate Veneers", Science and Art of Porcelain Laminate Veneers, 1st ed., pp. 318-323, London: Quintessence; (2003).

Peumans, et al., "Porcelain veneers bonded to tooth structure: an ultra-morphological FE-SEM examination of the adhesive interface", Dental Materials, vol. 15, pp. 105-119, (1999).

Jones, et al., "Effect of Etching Technique on the Clinical Performance of Porcelain Veneers", Quintessence of Dental Technology, vol. 10, No. 10, pp. 635-637, (1986).

Della Bona, et al., "Shear bond strength of resin bonded ceramic after different try-in procedures", J. Dent., vol. 22, pp. 103-107, (1994).

Hall, "Porcelain Veneer Procedure", on-line at http://www.mynewsmile.com/porcelainveneerprocedure.htm, 3 pages, (2013).

Patent Search Summary: Other Relevant Content, 10 pages, (2009).

The International Search Report for International Application No. PCT/IL22009/000769, 3 pages, mailed Nov. 9, 2009.

* cited by examiner

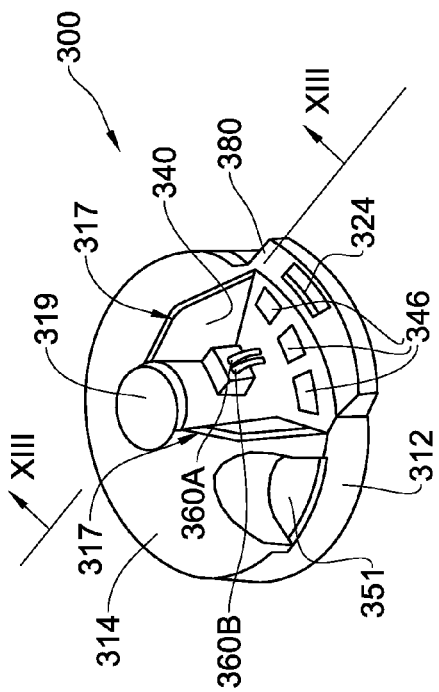
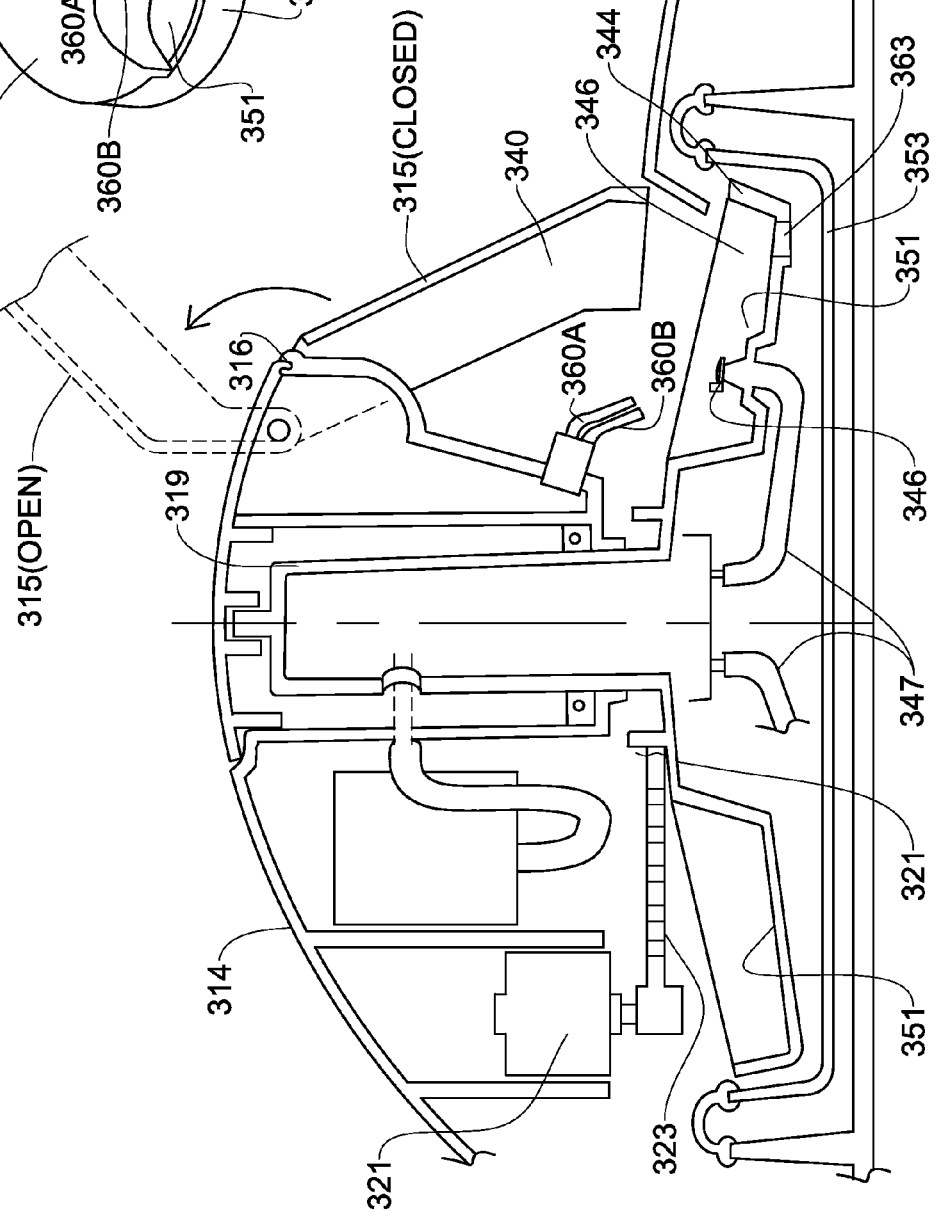

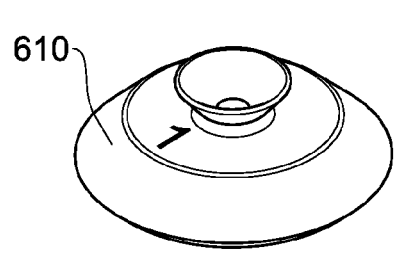
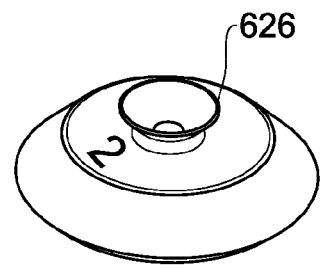
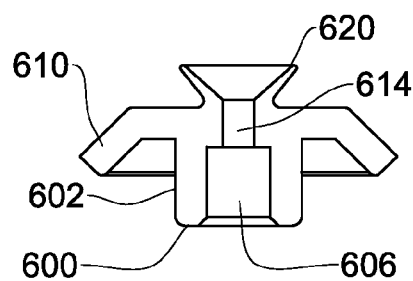
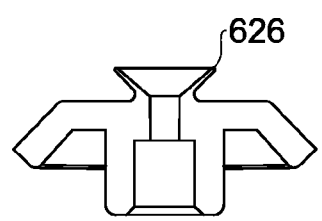
Fig. 23A                               Fig. 23B
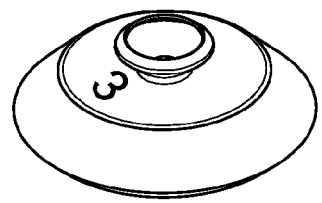
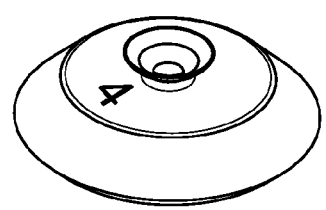
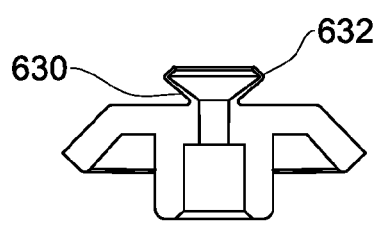
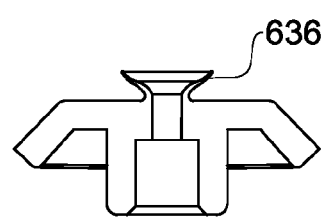
Fig. 23C                               Fig. 23D

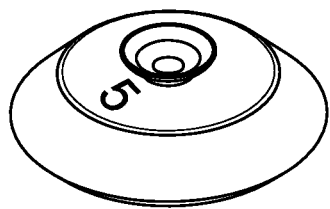
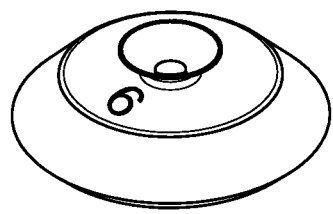
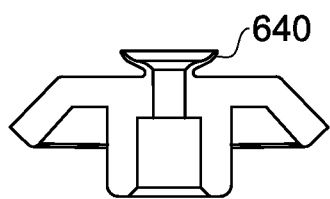
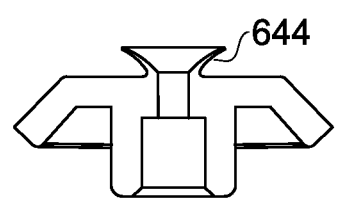
Fig. 23E
Fig. 23F
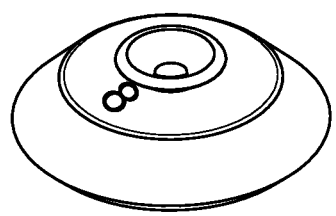
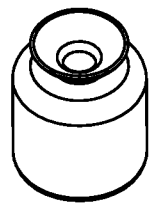
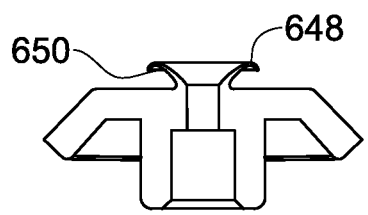
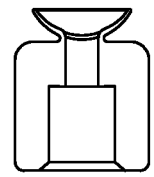
Fig. 23G
Fig. 23H

DENTAL RESTORATION CONDITIONING APPARATUS AND METHOD

This is a Continuation-In-Part of International PCT Application No. PCT/IL2009/0000769 filed on 6 Aug. 2009, and claims priority from U.S. patent application Ser. No. 61/136,012 filed on 6 Aug. 2008, the contents of which are hereby incorporated by reference in their entirety.

FIELD OF THE INVENTION

This invention relates to a dental restoration conditioning apparatus and method.

Hereinafter in the specification and claims the term dental restoration is used to denote any sort of coating applied over a tooth, or a tooth prosthesis, or an orthodontic implant, either for prosthetic or aesthetic dentistry, applied thereto by adhesion. A dental surface may be for example a veneer, ceramic inlays and onlays, crowns, bridges, and the like. A dental restoration may be made of a variety of material e.g. all-ceram crowns, ceramics, alumina, metal, zirconium, acrylic, porcelain, composite materials and the like.

BACKGROUND OF THE INVENTION

Dental esthetics is an ever-growing field among all disciplines in dentistry, designed to improve esthetic appearance of a patient's teeth. Aesthetic dentistry refers, among others, to treatment of teeth that are discolored, chipped, misshaped, or missing. Cosmetic treatment can reshape teeth, close gaps, restore worn or short teeth, and even change the length of teeth. An aesthetic restoration in many cases is carried out for cosmetic reasons only, though in some cases may also have functional aspects, e.g. in case of corrective dentistry.

Cosmetic dental techniques have advanced dramatically over the last decade. The quality of materials like porcelains and composite resins has improved, giving a more life-like appearance. This however requires also special treatment and care at the practitioners end during preparation of the dental restoration article prior to and while applying same to the individual's teeth.

US Patent Application 20070141530 to Neil John Graham is directed to a device for vacuum holding a dental veneer during the trial placement of a veneer on a tooth, application of adhesive to the veneer and final placement of the veneer on the tooth. The device includes a flexible suction cup with a connecting air bulb. The cup is placed on the external surface of the veneer while squeezing the air bulb. The veneer is held on the cup until the air bulb is squeezed. The instrument allows for multiple veneers to be simultaneously coated and placed.

U.S. Pat. No. 6,182,820 to Rathbauer John discloses a holder for dental implants namely dental veneers. The holder has a bottom tray and a top cover both opaque. The top cover has a recessed portion that is designed to receive a foam sheet. The foam sheet is designed to cover the top cover so that it blocks light from entering the closed holder. The bottom tray has recessed wells that are designed to receive dental veneers. When the cover is closed over the tray, the light is blocked out so that light-sensitive resin placed upon the dental veneers does not harden before the dental veneers are placed upon the patient's teeth.

U.S. Pat. No. 7,090,073 to Barnes is concerned with a dental tray assembly for storage of oral prosthetics includes a base and a cover, associated with the base and being configured to be alternately positioned relative to the base in a first, closed position, and a second, open position. A biasing element interconnects the base and the cover to provide a biasing force between the cover and the base, the biasing force varying with position of the cover relative to the base to provide an attractive force between the cover and the base when the cover is in the first, closed position, and a repellant force between the cover and the base when the cover is in the second, open position. A storage tray is nestable within the base, the storage tray including at least two compartments, each compartment being configured to receive and store an oral prosthetic therein.

SUMMARY OF THE INVENTION

The present invention aims at providing an apparatus for efficiently performing preparatory procedures on a dental restoration, namely conditioning it after manufacturing however prior to adhesion over individual's teeth.

The present invention, according to a first aspect thereof, is directed to a dental restoration conditioning apparatus comprising a housing formed with at least one confined dental restoration treating space, said housing fitted with at least one dental restoration grip, and at least one fluid applying nozzle, wherein at least one of said at least one dental restoration grip and at least one fluid applying nozzle is displaceable with respect to an other of said dental restoration grip and at least one fluid applying nozzle; a supply of at least one fluid agent being in flow communication with said fluid applying nozzle, a fluid drain from said confined space, and a programmable controller.

According to another aspect, the present invention is directed to a method for conditioning a surface of a dental restoration, the method comprising the following steps:

(a) Obtaining a dental restoration conditioning apparatus comprising a housing formed with at least one confined dental restoration treating space, said housing fitted with at least one dental restoration grip, at least one fluid applying nozzle, wherein at least one of said at least one dental restoration grip and at least one fluid applying nozzle is displaceable with respect to an other of said dental restoration grip and at least one fluid applying nozzle; a supply of at least one fluid agent being in flow communication with said fluid applying nozzle, a fluid drain from said confined space, and a programmable controller;

(b) Securely applying a dental restoration on the dental restoration grip;

(c) Activating the controller to generate control signals for a conditioning process;

(d) Removing the dental restoration.

Any of at least one of the following features and designs are applicable for use in connection with the different aspects of the present invention:

- the housing is fitted with a plurality of treating spaces, each fitted with a dental restoration grip and at least one fluid applying nozzle, wherein each such treating space is suited for performing independent sequence of operations on a dental restoration received therein.
- the dental restoration grip is a resilient vacuum/suction cup.
- the dental restoration grip is an array of dental restoration grips locations, each corresponding with at least a portion of a dental array of teeth, as disposed in a human's mouth.
- the array of dental restoration grips is disposed along a linear path or over a curved/circular path.
- the fluid applying nozzle is displaceable so as to cooperate with each location at the array of dental restoration grips.

the at least one fluid applying nozzle is displaceable at least about a first axis, transversing said linear array of locations.

where a plurality of fluid applying nozzles are provided, they may be suited for performing sequential conditional operations over a plurality of dental restoration grips locations.

the array of dental restoration grips is disposed on a carousel-like tray and wherein one or both of the array of locations and the at least one fluid applying nozzle are rotatable with respect to one another.

the supply of at least one fluid agent comprises at least one of fresh water supply, air/gas supply (pressurized or suction) and at least one surface treating agents supply.

the supply of at least one fluid agent is via disposable cartridges attachable to the apparatus.

the fluid drain is in flow communication with a disposable waste container articulated with the apparatus.

selective heating is provided for selectively heating at least one of the fluid agents. For example, heating rinsing liquids or drying air.

the confined dental restoration treating space is fitted with a protective door, said door being formed with at least visor portion for visualizing the confined dental restoration treating space.

the visor portion is fitted with a selective spectrum light filter to prevent un-intended light curing.

the apparatus may further comprise an internal illumination source.

the apparatus may further comprise a light source for selective and controllable light curing.

the surface treating agent is at least one of a sand blasting agent, coating agent, etching/abrasive agent.

each of the dental restoration grip locations is associated with an individual fluid applying nozzle.

the housing is fitted with a switch associated with the door, whereby opening the door instantaneously halts operation of the apparatus.

the dental restoration grip is replaceable so as to conform with various shapes and sizes of dental restorations.

the apparatus may further comprise an ultrasonic transducer to enhance penetration of the applied fluids also to fine pores, thereby improve surface treating.

during a conditioning process partitioning is provided between neighboring dental restoration grips, to thereby prevent splashing of agent therebetween.

partitions are integrated with the at least one fluid applying nozzle or with the dental restoration grip locations.

the partition is in the form of a dome-like closure fitted over the at least one fluid applying nozzle.

the partition is in the form of a ell-like receptacle associated with each dental restoration grip location.

the dental restoration grip is fitted with a vacuum actuating mechanism whereby such vacuum is applied only upon presenting a dental restoration over a respective vacuum cup. Alternatively, the vacuum to each vacuum cup is manually activated.

the controller provides audio/visual alerts regarding a conditioning process.

the controller provides indicia representative of the conditioning process for each dental restoration.

the conditioning process includes some or more of the steps of rinsing, drying, sand blasting, etching, and applying adhesive material.

a substance applicator may be associated with at least one nozzle, for fine application of material, e.g. adhesive material. The applicator is for example in the form of a brush, a sponge-like applicator, etc.

the dental restoration grip may be coupled with an applicator for applying the dental restoration at an individual's mouth. The applicator may be integral with the dental restoration grip or be attachable thereto.

the housing is fitted with a basin and wherein the dental restoration grip is displaceable to/from said basin for performing operations such as rinsing, ultra-sonic treatment of the dental restoration, etc.

the dental restoration grip is displaceable between a loading/unloading position wherein the dental restoration is loaded or unloaded on a grip, and a treating position wherein the dental restoration is firmly gripped by a grip and is manipulated by the unit. According to a particular design, access to the dental restoration is possible only when the dental restoration grip is at the loading/unloading position. Furthermore, at the treating position the dental restoration grip is at a lower position, i.e. received within the basin, whilst at the loading/unloading position the dental restoration grip is at a position elevated from said basin, such that a dental restoration griped thereby is readily accessible.

displacement of the dental restoration grip between the loading/unloading position and treating position is facilitated by a cam/follower mechanism associated with the dental restoration grip and a partition wall extending between neighboring treating spaces.

According to another aspect of the invention, the dental restoration grip is a resilient vacuum/suction cup, it has a housing formed with a flow path culpable to a suction source, with a substantially resilient grip, typically made of resilient material such as silicone rubber or the like, wherein said grip has an open gripping edge, and having at least one of the following features:

(a) the grip has substantially an inverted dome-like shaped section;
(b) the grip has a conical cross-section;
(c) the grip has a concave cross-section;
(d) the grip has a convex cross-section;
(e) the gripping edge of the grip has a smooth peripheral lip, said lip being thinner than the domed portion;
(f) the lip is circular or slightly oval;
(g) the lip converges inwardly or it may diverge outwardly.

The dental restoration grip may be formed with a skirt-like portion for protection concealment of a holder thereof. This is in particular useful when sand blasting is to be applied to the restoration grip and thus the skirt-like portion protects the grip holder from wear during the sand blasting procedure. Thus, the dental restoration grip may be also formed without said skirt portion and may be coupleable in different forms to a vacuum source.

A controller associated with the apparatus according to the invention is programmable whereby one may enter a series of conditioning parameters such as: sequence of operations, duration of each operation, amount of fluid applied during each operations, heating temperature, flow rate, type of alert signal (audio and/or visible).

According to another aspect of the presently disclosed subject matter, there is provided a dental restoration conditioning apparatus comprising a housing formed with a liquid-tight dental restoration treating space comprising a liquid drain, said housing configured with a disposable dental restoration grip comprising at least one resilient vacuum cup, each of said at least one vacuum cups being in flow communication with at least one vacuum source.

According to another aspect, the present invention is directed to a method for conditioning a surface of a dental restoration, the method comprising the following steps:
  (a) Obtaining a dental restoration conditioning apparatus comprising a housing formed with a liquid-tight dental restoration treating space comprising a liquid drain, said housing configured with a disposable dental restoration grip comprising at least one resilient vacuum cup, each of said at least one vacuum cup being in flow communication with at least one vacuum source, and a programmable controller;
  (b) Securely applying a dental restoration on the resilient vacuum cup;
  (c) Activating the controller to generate control signals for a conditioning process; and
  (d) Removing the dental restoration.

Any of at least one of the following features and designs are applicable for use in connection with the different aspects of the present invention:
  the disposable grip is a uniform array fitted with said at least one resilient vacuum cup;
  the disposable grip is constituted of a plurality of disposable individual grips each fitted with a resilient vacuum cup;
  each of said at least one vacuum cups are in fluid communication with their corresponding at least one vacuum sources;
  said at least one vacuum cups are connected to a single vacuum source;
  the apparatus further comprises at least one fluid applying nozzle, wherein at least one of said at least one vacuum cups and at least one fluid applying nozzle is displaceable with respect to another of said at least one vacuum cups and at least one fluid applying nozzle, and a supply of at least one fluid agent being in flow communication with said fluid applying nozzle;
  the housing is fitted with a plurality of treating spaces, each fitted with a vacuum cup and at least one fluid applying nozzle, wherein each such treating space is suited for performing independent sequence of operations on a dental restoration received therein;
  the fluid applying nozzle is displaceable so as to cooperate with each location of said at least one vacuum cups;
  said at least one vacuum cups are disposed on a carousel-like tray and wherein one or both of the cups and the at least one fluid applying nozzle are rotatable with respect to one another;
  the supply of at least one fluid agent comprises at least one of fresh water supply, air supply and surface treating agent supply;
  the apparatus further comprises a programmable controller;
  the liquid drain is in flow communication with a disposable waste container articulated with the apparatus;
  the treating space is fitted with a protective door, said door formed with at least visor portion for visualizing said treating space;
  the apparatus further comprises an internal illumination source;
  the apparatus further comprises a light source for selective and controllable light curing;
  the vacuum cup is replaceable so as to conform with various shapes and sizes of dental restorations;
  during a conditioning process partitionings are provided between neighboring vacuum cups, to thereby prevent splashing of agent therebetween; and
  during a conditioning process partitioning is provided between neighboring vacuum cups, to thereby prevent splashing of agent therebetween.

BRIEF DESCRIPTION OF THE DRAWINGS

In order to understand the invention and to see how it may be carried out in practice, embodiments will now be described, by way of non-limiting examples only, with reference to the accompanying drawings, in which:

FIG. 12 is a schematic perspective view of a carousel-type apparatus in accordance with an embodiment of the present invention;

FIG. 13 is a section along line XIII-XIII in FIG. 12;

FIGS. 22A to 21C are isometric views corresponding with FIGS. 20A to 21C;

FIGS. 23A to 23H illustrate different forms of dental restoration vacuum cups used in accordance with the present invention;

DETAILED DESCRIPTION OF SPECIFIC EMBODIMENTS

Figure 1:
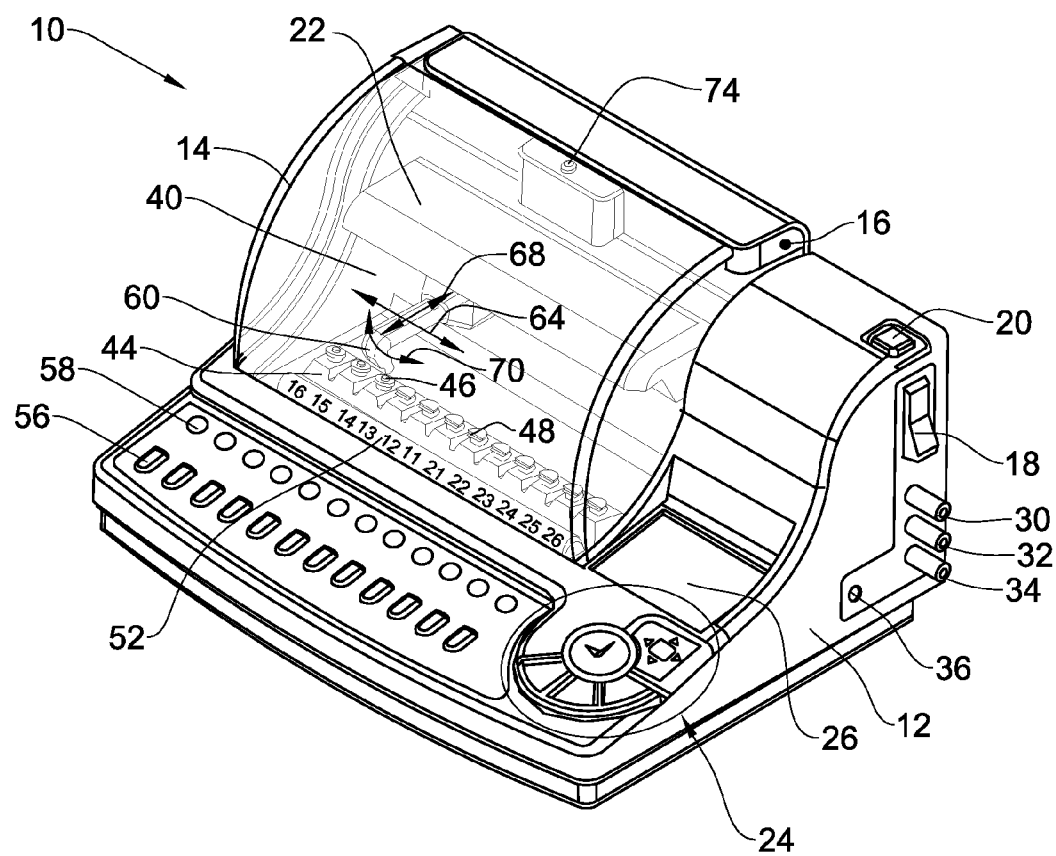
FIG. 1 is an isometric view of a dental restoration conditioning apparatus in accordance with a first embodiment of the present invention, with the lid at its closed position.
Figure 2:
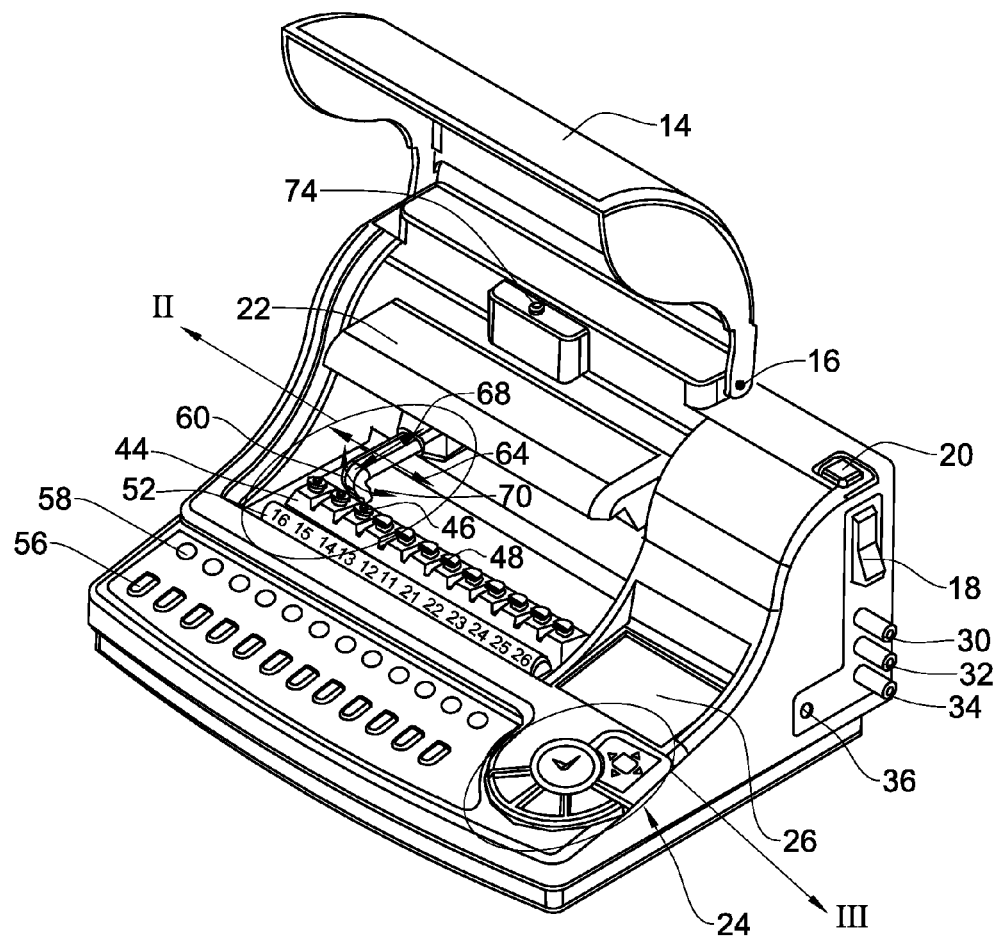
FIG. 2 illustrates the apparatus for FIG. 1 with the lid at its open position.

Turning first to FIGS. 1 to 3 there is illustrated a dental restoration conditioning apparatus in accordance with an embodiment of the present invention generally designated 10. The apparatus 10 comprises a housing 12 sized suitably for being a desk top device and fitted with a lid 14 pivotable with respect to the housing at 16 between a closed position (FIG. 1) and an open position (FIG. 2). The housing is fitted with a main power switch 18 displaceable between ON/OFF positions, shutting down all the systems of the apparatus. The apparatus further comprises a light switch 20 for activating an internal light 22. It is however appreciated that the illuminator assembly may comprise two independent light sources one being visible light e.g. fluorescent light and the other being a curing light source at a specified wavelength depending on the required performance.

Housing 12 is further fitted with a set of operating knobs 24 (seen at enlarged view of FIG. 3B) and further there is provided a display panel 26 on which one may view the status of the procedure being held and further useful in setting the parameters of a procedure.

The housing 12 is fitted with a first inlet port 30 connectable to a pressurized air source (not shown) a water supply port 32 connectable to a fresh water supply (not shown) and a third inlet 34 connectable to a supply of any suitable treating agent (not shown) e.g. etching agent etc. A drain port 36 is provided connectable to a drain container or directly to the drain of a sink, for example (not shown). It is appreciated that further inlet ports may be provided depending on the required procedure, namely the number of agents required for a particular procedure. Alternatively, one of the inlet ports, typically the third inlet port, may be selectively coupled to different supply sources.

The lid 14 together with the housing 12 define a confined dental restoration treating space 40 fitted with a dental restoration grip generally designated 44 and comprising an array of vacuum cups 46 each suited for vacuum gripping of a dental restoration 48. The lid may be treated so as to prevent/admit only certain wavelengths of light therethrough, e.g., to prevent day light through the lid to thereby avoid spontaneous curing of the materials applied over the dental restoration.

It is noticed that the dental restoration grip 44 has an indexing bar 52 which may be used to index the dental restorations in accordance with the location within an individual's mouth and be identified as upper/lower jaw, as common in the dentistry art. It is further noticed that in this particular embodiment the dental restoration grip 44 is a uniform array though in accordance with other embodiments of the invention each suction grip may be an independent resilient vacuum cup which may be easily replaced to suit different sizes of dental restorations as well as different shapes thereof (e.g. makes rendering it suitable for use in conjunction with veneers, crowns, inlays, onlays, bridges and the like). The housing 12 is further fitted with a plurality of activating knobs 56, each corresponding with a respective dental restoration grip 46 and further with an indicator 58 typically in the form of an LED indicating the state of a particular dental restoration grip.

Received within the confined dental restoration treating space 40 there is a fluid applying nozzle 60 which in the present example is slideably displaceable in two axes and in the first axis represented by arrow-head 64 extending parallel to the linear array of dental restoration grip 44 and in a second direction, perpendicular thereto, as represented by arrowed line 68 transversing the first direction. Optionally, the fluid applying nozzle 60 may further have another degree of freedom in a pivotal direction as represented by arrowed line 70. The degrees of freedom imparted to the fluid applying nozzle 60 render it accessible to each dental restoration for performing a wide variety of operations as required and as will be mentioned hereinafter.

As can further be seen, within the confined space 40 there is provided a safety switch 74 engageable by the lid/cover 14 whereby opening the lid (FIG. 2) instantaneously stops any operation of the apparatus and generates a corresponding signal to the programmable controller of the device (not seen).

It is seen that the lid 14 is made translucent, though in accordance with other embodiments (not shown) it may have only a transparent window portion allowing visualizing the dental restoration grip portion 44.

The vacuum cups 46 of the dental restoration grip 44 may be activated by a contact sensor or by an IR detector or by means of operating knobs 56. Likewise, stopping the active grip of a dental restoration applied over a resilient vacuum cup 46 is carried out by pressing anyone of the corresponding knobs 56.

The apparatus is further provided with a heating unit (not seen) for heating any of the fluids applied to the apparatus (i.e. air, rinsing water or any other of the other applied liquid agents). However, in accordance with other embodiments of the device, hot air may be a priori supplied.

The apparatus is fitted with an ultra sonic transducer (not seen) for imparting the dental restoration with vibrations to thereby increase penetration of the liquids/agents applied thereto, thereby enhancing cleaning. The ultra sonic treatment is useful for example in cleaning micro-pores on the dental restoration surface.

Figure 3A:
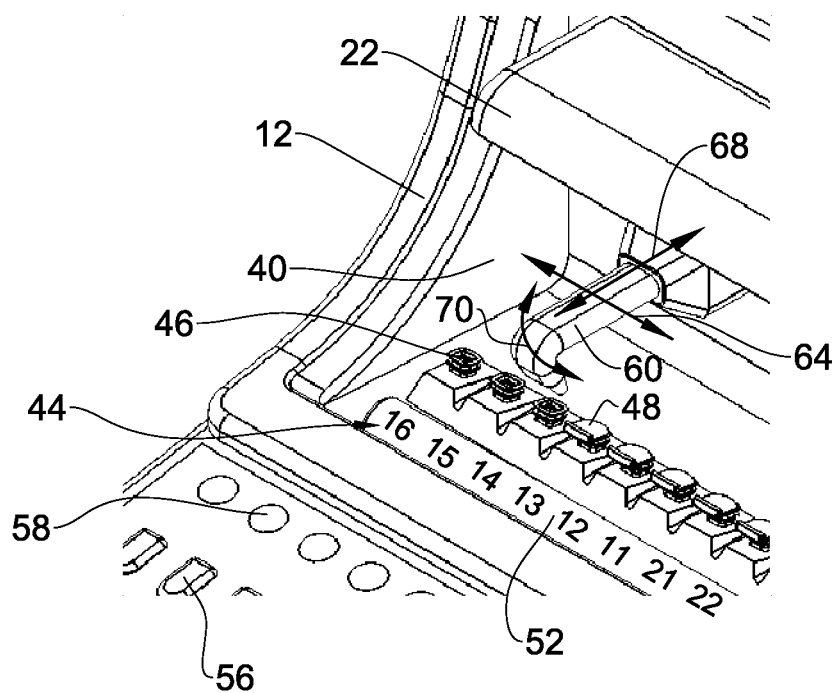
FIG. 3A is an enlargement of the portion marked II in FIG. 2.
Figure 3B:
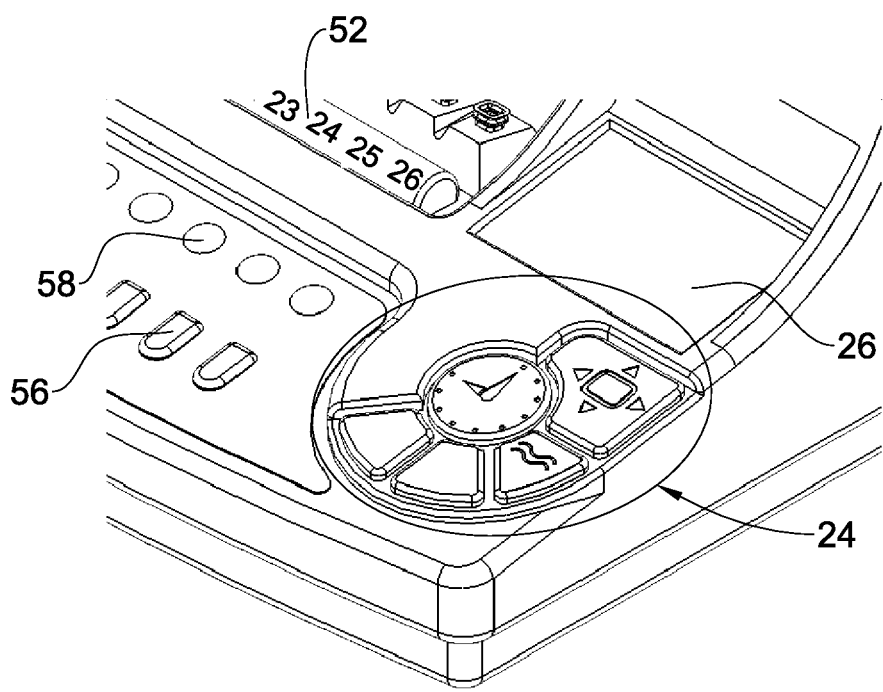
FIG. 3B is an enlargement of the portion marked III in FIG. 2.
Figure 3C:
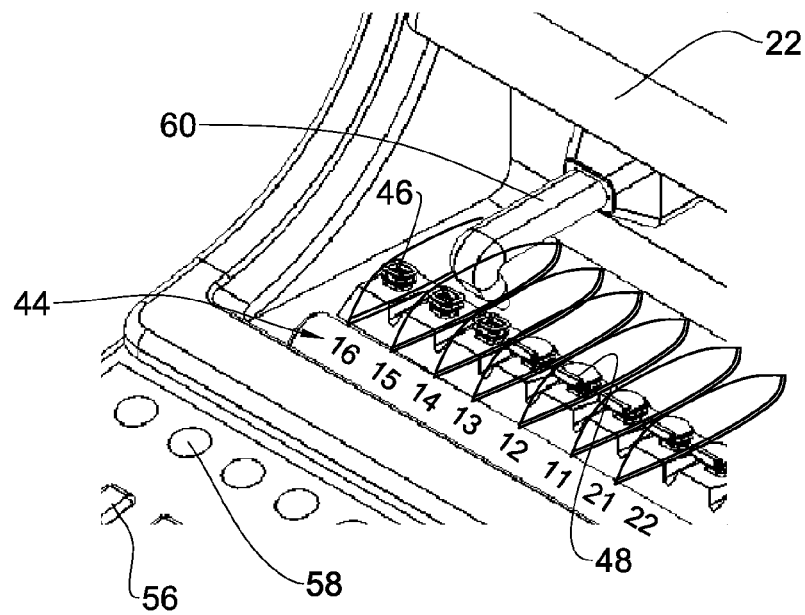
FIGS. 3C and 3D illustrate embodiments of shielding arrangements used in conjunction with the apparatus.
Figure 3D:
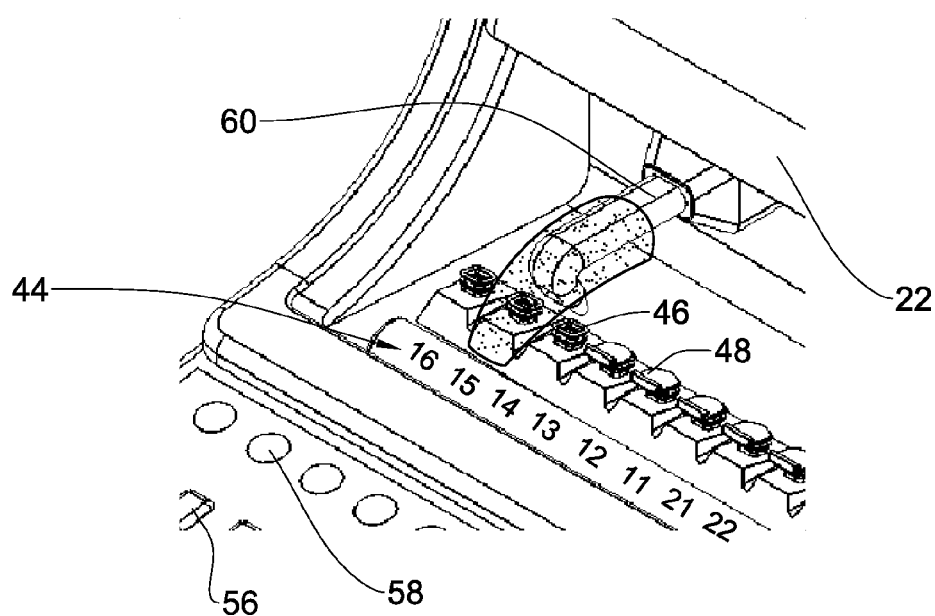

In order to prevent splashing of any fluids while treating a dental restoration fitted over one location of the dental restoration grip 44, at least one protective shield may be provided in accordance with several configurations. For example, a protective shield may be mounted over the displaceable fluid applying nozzle 60 such that the shield displaces along with the nozzle. In accordance with another embodiment, each location at the dental restoration grip 44 is fitted with a shield whereby the fluid applying nozzle 60 travels between the shields so as to apply fluid over a particular dental restoration received within a particular location, however without affecting neighboring dental restorations applied over neighboring resilient vacuum cups (FIGS. 3C and 3D respectively).

The programmable controller may be programmed to carry out different tasks, depending on the nature of the dental restorations used and the specific procedure associated therewith. For example, the controller may be programmed to automatically carry out a sequence of operations, though it may be manually interrupted at any time with an internal clock governing the procedures which often require precise timing. The controller may be programmed to perform tasks such as cleaning with a jet of pressurized air, rinsing with water or other liquid, spraying with a solution, drying with warm air, applying different chemical agents such as etching agents, adhesive/bonding agents, etc. The controller is programmable to determine the sequence of any such operations, their duration, intensity of jets applies, heating temperature, etc.

Figure 4:
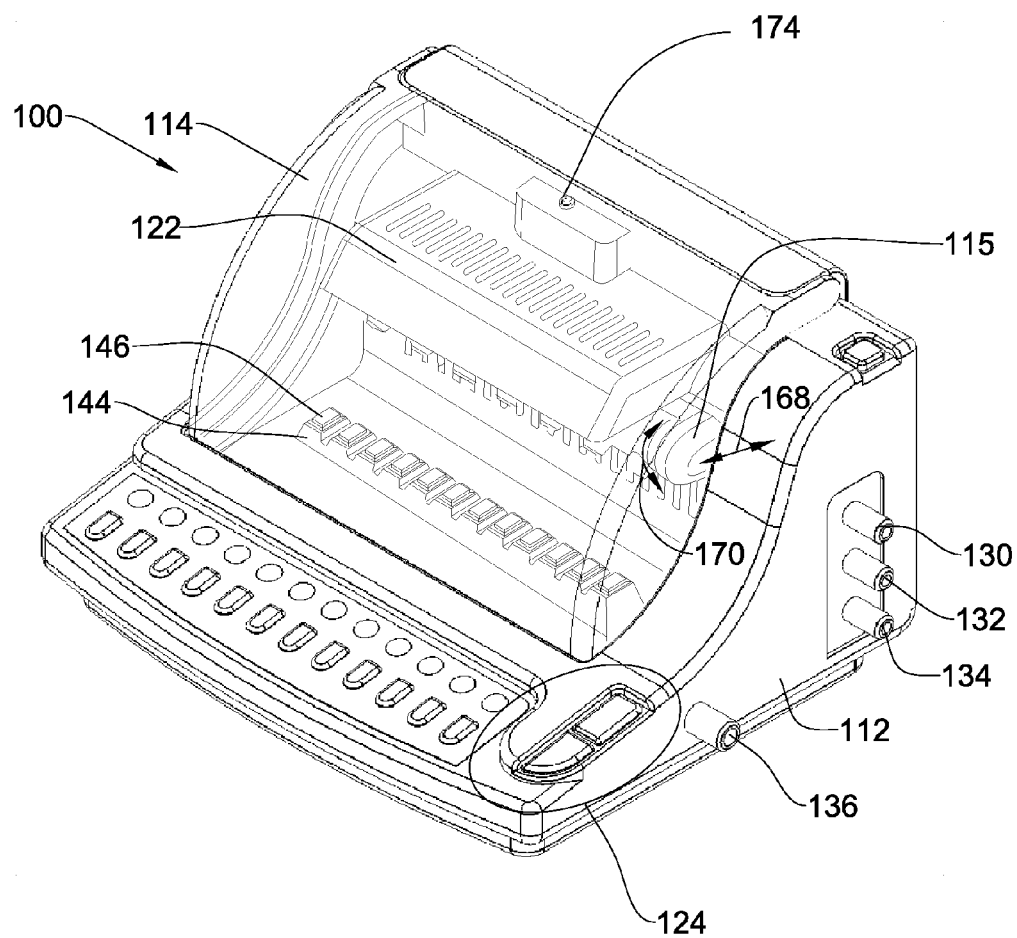
FIG. 4 is a modification of the apparatus of FIG. 1, with the lid closed.
Figure 5:
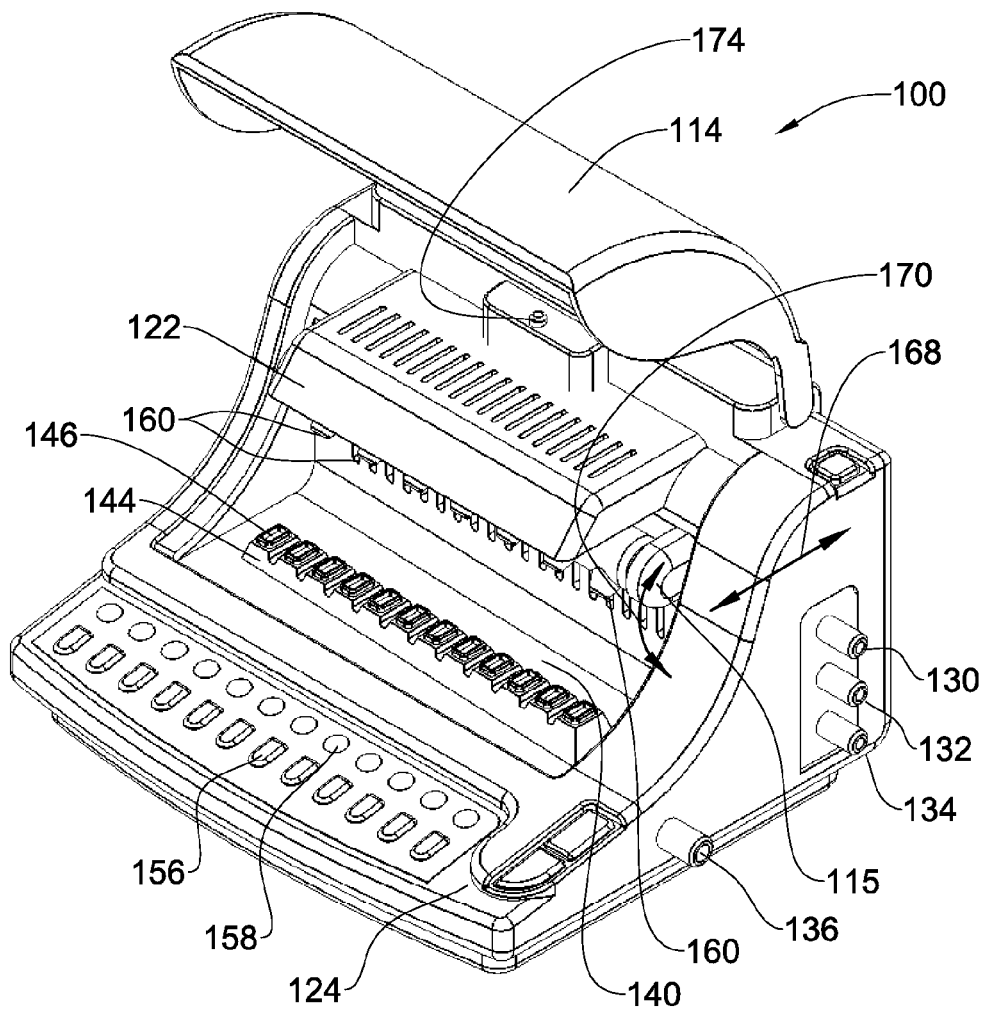
FIG. 5 illustrates the apparatus of FIG. 4 with the lid open.
Figure 6:
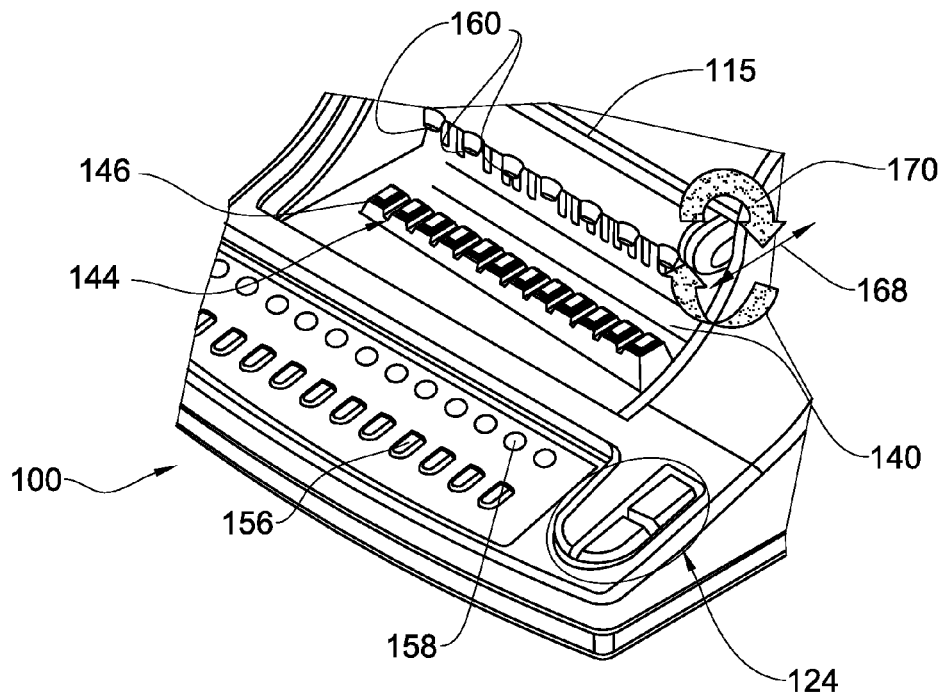
FIG. 6 illustrates a modification of the apparatus seen in FIG. 5.
Figure 7:
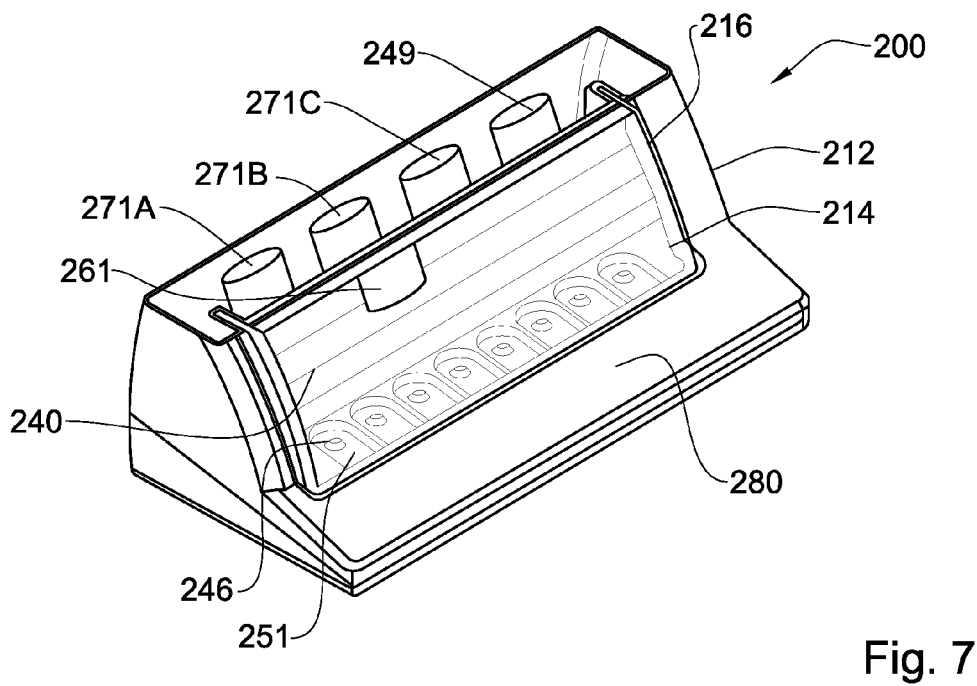
FIG. 7 is an isometric view of still another embodiment of the apparatus according to the present invention with the lid at its closed position.
Figure 8:
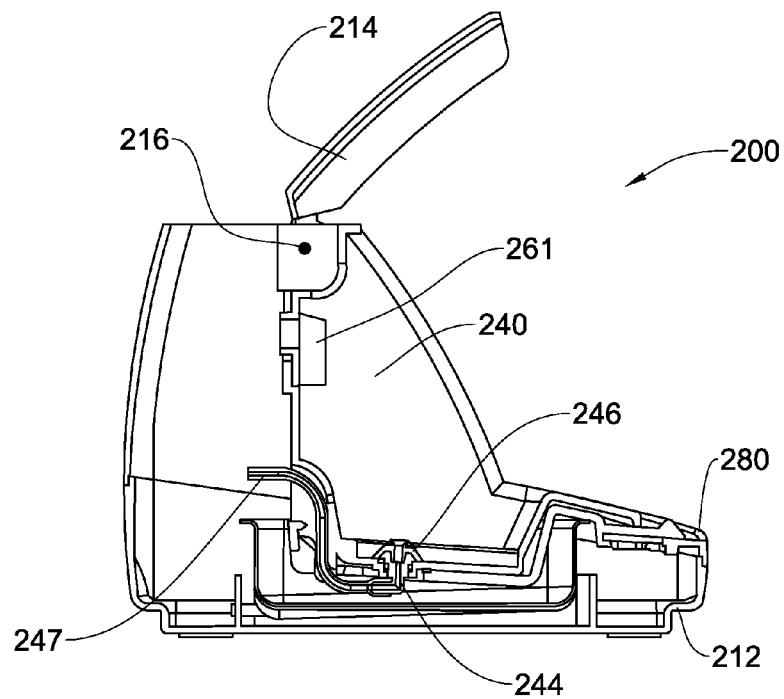
FIG. 8 is a side view of the apparatus of FIG. 7, with the lid at its open position, also showing from internal components.

Turning now to the embodiment of FIGS. 4 to 6 there is illustrated a variation of the dental restoration conditioning apparatus in FIGS. 1 to 3. The embodiment now generally designated 100 is substantially similar to the previous embodiment and accordingly, like elements have been designated with like reference numerals however shifted by 100.

The apparatus 100 has a housing 112 fitted with a programmable controller (not seen) and fitted with operating knobs 124. Whilst the housing is fitted with optional inlet ports namely air inlet port 130, water inlet port 132 and liquid agent port 134, those are optional as the apparatus 100 is fitted with an internal waste container, an internal water container, an internal liquid agent container and a cylinder of compressed air, neither of which being seen however all being replaceable and may be provided in the form of a kit for use with the apparatus. The apparatus 100 is also fitted with an internal heating chamber for heating air (for purposes of drying the dental restorations) or the water (for rinsing thereof).

It is realized that whilst a drain port may be provided (similar to port 36 in the previous embodiment) it would be advantageous to maintain the waste drain liquid within a waste container, rather than disposing of such liquids to the sewage, so as to be environmental friendly.

In addition, it is noticed that rather than the individual liquid applying nozzle (best seen in the previous embodiments) in the present embodiment the apparatus 100 is fitted with a multi-fluid applying nozzle head generally designated 115 and provided with a plurality of fluid applying nozzles 160 (best seen in FIG. 6) the arrangement being such that each location of the dental restoration grip 140 faces a corresponding fluid applying nozzle 160. In order to provide adequate fluid (liquids or gaseous material) over the treated dental restoration mounted on the respective vacuum cups 146 the head 115 is linearly displaceable in direction of arrowed head 168 and is further pivotable about its longitudinal axis in direction of arrows 170.

According to this embodiment, the dental restorations mounted on the respective dental restoration grip are treated simultaneously though it is appreciated that through each of the respective nozzles 160 different substances may be applied. For example, while several dental restorations may be dried using air, other dental restorations may be rinsed while other dental restorations may be etched by a suitable etching agent applied thereon.

Similar to the previous embodiment, it is advantageous to provide a shielding arrangement to prevent splashing of liquids from one dental restoration to a neighboring restoration. This may be carried out by either providing a plurality of shields each associated with a location of the dental restoration grip or with providing such shields each associated with the respective fluid applying nozzles 160.

Turning now to FIGS. 7 to 11 there is illustrated still an embodiment of a dental restoration conditioning apparatus in accordance with an embodiment of the application, generally designated 200 wherein for sake of clarification, like elements are designated with like reference numbers as in connection with the embodiment of FIGS. 1 to 3, however shifted by 200.

The housing 212 in accordance with this embodiment is formed with a confined dental restoration treating space 240 accessed through a pivotable lid/cover with respect to the housing at 216. The apparatus is fitted with a dental restoration grip 244 comprising a plurality of resilient vacuum cups 246. As can be seen in particular in FIG. 9, the vacuum cups 246 are replaceable (to conform with different size and shape of dental restorations) and said resilient cups are mounted over a substantially rigid grip seat 245 coupled to a suction line 247.

As can further be seen in the drawings each of the vacuum cups is received within a receptacle in the form of a basing 251 constituting a shielding arrangement to prevent splashing/contamination of neighboring dental restorations.

Figure 9:
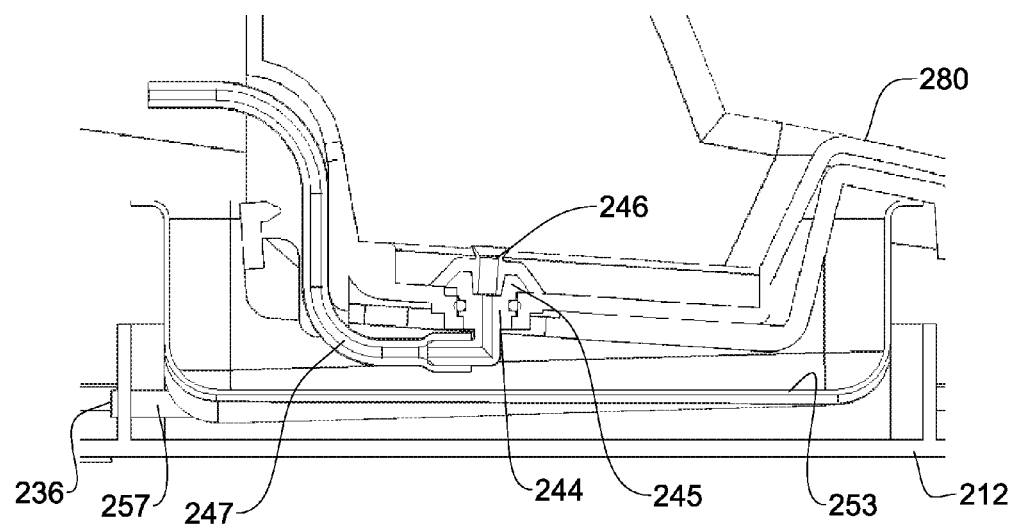
FIG. 9 is an enlargement of a lower portion of the apparatus seen in FIG. 8.

The apparatus comprises a removable basing 253 (FIGS. 8 to 10) formed at its lower end with a drain port 257 extending out to the drain port 236 (FIG. 9).

Figure 10:
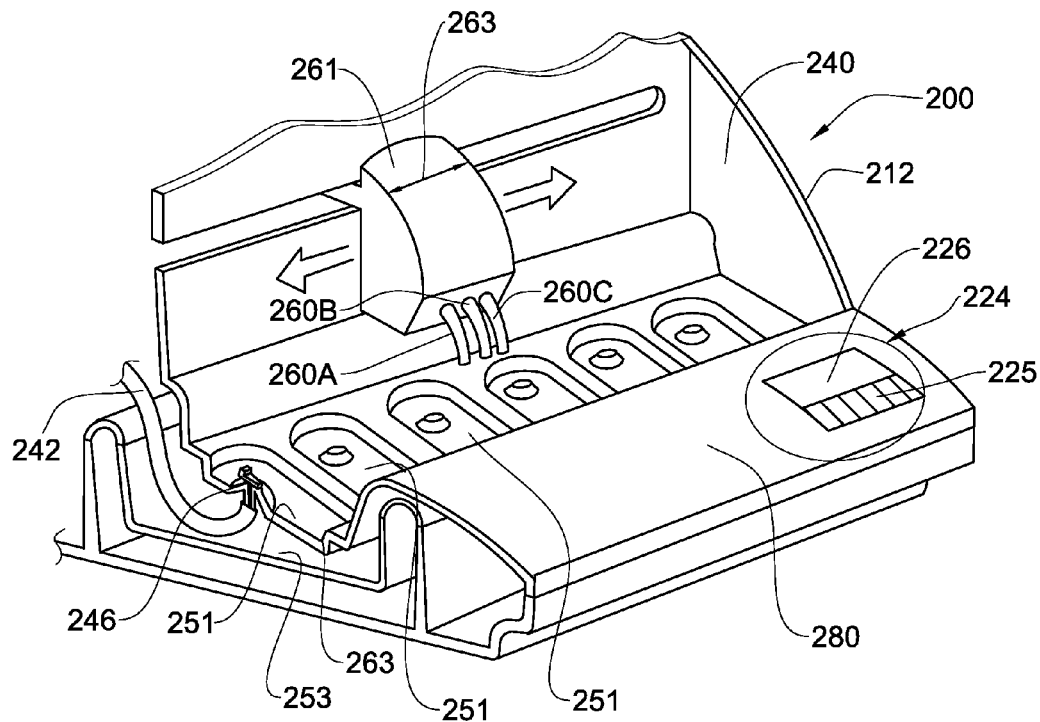
FIG. 10 is a partially sectioned isometric view of a front lower portion of the apparatus seen in FIG. 7, with the lid at its open position.

As can be seen, best in FIG. 10, the apparatus in accordance with the present embodiment comprises an axially displaceable carriage 261 slideable in direction of arrowed line 263. The carriage 261 is formed with three fluid applying nozzles 260A, 260B and 260C, coupled to respective water container 271A, pressurized air cylinder 271B and a treating agent 271C, respectively. However, in accordance with a modification, rather than three separate fluid applying nozzles there may be provided only one such nozzle selectively connectable to each of said containers. Further containers may be introduced, depending on the particular model of apparatus and the intended procedure.

The apparatus 200 is further provided with a wrist support designated at 280 whereby the practitioner may comfortably place his wrist thereover and perform accurate manipulations on the dental restorations in a sturdy manner. Such an operation may be for example sand blasting by a sand blasting device 291 (FIG. 11) fitted with a sand blasting nozzle 293 coupled via supply line 295 to a pressurized source of blast a blasting agent. The nozzle 293 is received within a dome-shaped cover 297 formed at its end with a bellows like protection skirt 299 to be placed over the dental restoration 248 fitted over the respective resilient vacuum cup 246. The arrangement is such that during performing a sand blasting procedure no material is scattered within the confined treating space 240, which material is then drained through apertures 263 formed in each depression 251 as discussed hereinabove.

It is appreciated that other features of the embodiment illustrated in FIGS. 7 through 10 are substantially similar to those discussed in connection with the previous embodiments and the reader is directed thereto. For example, there is provided an internal rate collecting container designated 249 (FIG. 7) wherein all waste liquid and particles are collected therein and may then be removed and properly disposed of in a user friendly and environmentally friendly manner.

Furthermore, the device is fitted with a programmable controller which in the particular case is positioned below the wrist support 280 and is programmable and controllable via control panel 224 via the display panel 226 and the plurality of panel operating knobs 225.

The embodiment illustrated in FIGS. 12 to 16 is concerned with a dental restoration conditioning apparatus in accordance with a modification of the invention generally designated 300, wherein like components as discussed in connection with the first embodiment of FIGS. 1 to 3 are designated with like reference numerals however shifted by 300.

The apparatus 300 is a carousel-type device wherein as opposed to the linear configuration of the previous embodiments, in this embodiment the configuration is circular and operation is carried out in a carousel-type device.

The apparatus is seen generally in FIG. 12 and comprises a housing 312 fitted with a domed lid 314 defining beneath it a confined dental restoration treating space 340. The lid 314 is fitted at a front portion thereof with a sector-like aperture 317 allowing access to "in duty" dental restoration grips 346.

A central post 319 extends from the base 321 and serves both for supporting the domed lid 314 and for supporting supply lines extending to the various fluid applying nozzles 360A and 360B extending within the sectorial opening 317 and further supporting other nozzles extending within the confined space for simultaneous treating of several dental restorations received within stand-by dental restoration grip locations (not extending within the sector 317).

It is appreciated that the sector portion 317 is closeable by a tiltable lid 315 pivotable to the main lid 314 at 316.

A basin-line tray 353 is provided within the housing 312 from which an outlet LED drain extends towards a drain port (not seen). A carousel-like dental restoration grip 344 is rotatable within the housing 312 by means of an electric motor 321 engaged for rotation thereof by means of a drive belt 323 so as to rotate the carousel 344 in the required direction in accordance with sequence of conditioning operations, controllable by the programmable controller 324.

Similar to the embodiment illustrated in connection with FIGS. 7 to 10, each dental restoration grip 346 is formed within a respective well 351 formed with a drain opening 363 extending into the waste basin 353. Each resilient vacuum cup 346 is coupled via vacuum line 347 to a vacuum source for drain of waste liquid and debris.

Figure 11:
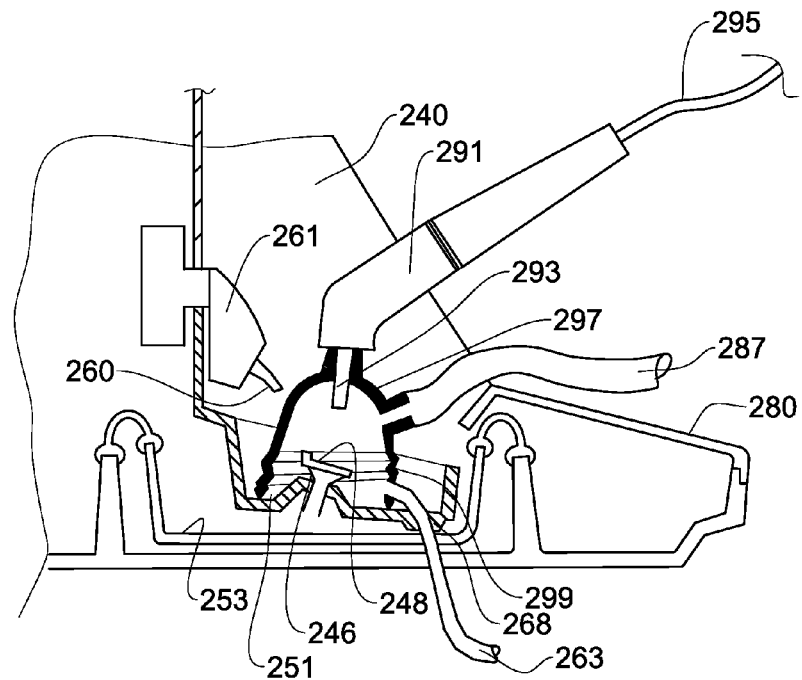
FIG. 11 is a sectioned side view of a portion of the apparatus illustrating a sand blasting procedure.
Figure 16:
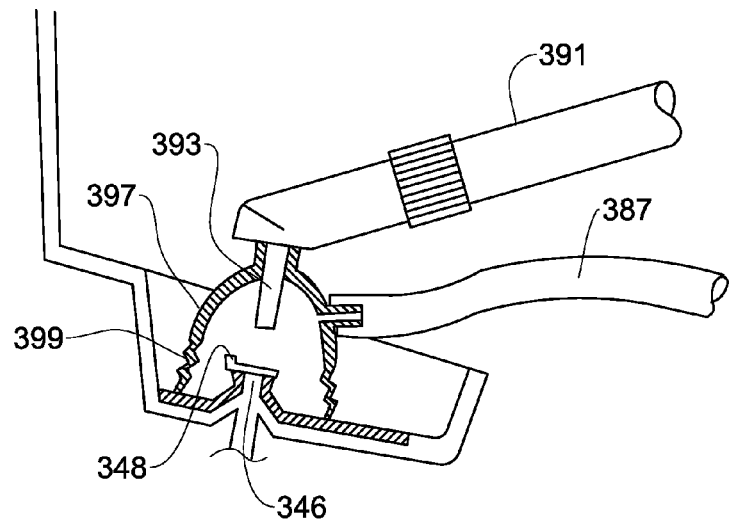
FIG. 16 is a section side view illustrating how the device of FIG. 12 is used during a sand blasting procedure.

The lid 314 is formed with a side opening 351' through which special procedures may be manually performed e.g. sand blasting as can be seen in FIG. 16 wherein a sand blaster device 391 is provided fitted at its fore-end with a sand blasting nozzle 393 which like in the embodiment of FIG. 11 comprises a domed-shaped protective cover 397 with a bellows-like open end 399 and a suction tube 387 extending therefrom. The device may be applied over a dental restoration 348 mounted over a respective vacuum cup 346 to thereby perform a sand blasting procedure however without effecting neighboring dental restorations received in neighboring depressions of dental restoration grips.

Figure 17:
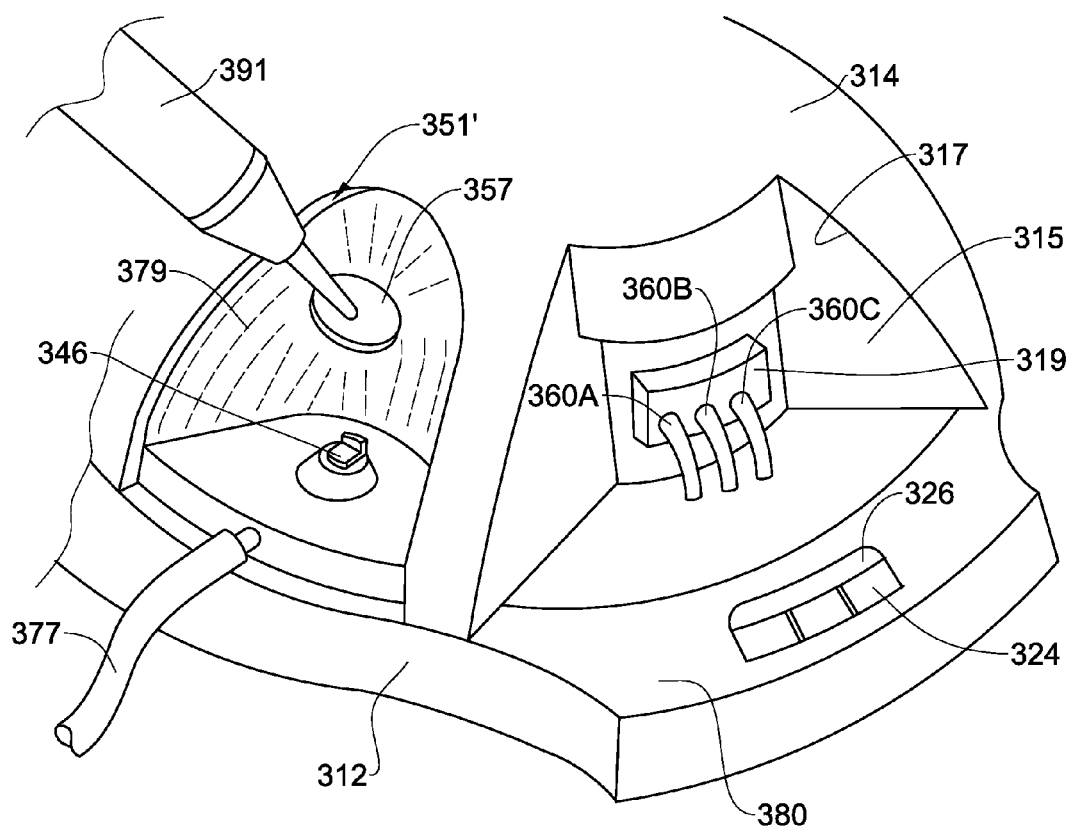
FIG. 17 illustrates a variant sand blast operation performed with a carousel-type apparatus of the present invention.

FIG. 17 illustrates a modification of the arrangement discussed in conjunction with FIG. 16 wherein a specially designated suction line 377 is provided for withdrawal of any waste liquid and debris generated during performing of a procedure through the side opening 351'. In this particular case the side opening 351' is fitted with a protective visible shield 379 formed with an aperture 357 through which a manually held manipulator e.g. sand blaster 391 may be produced.

Figure 14:
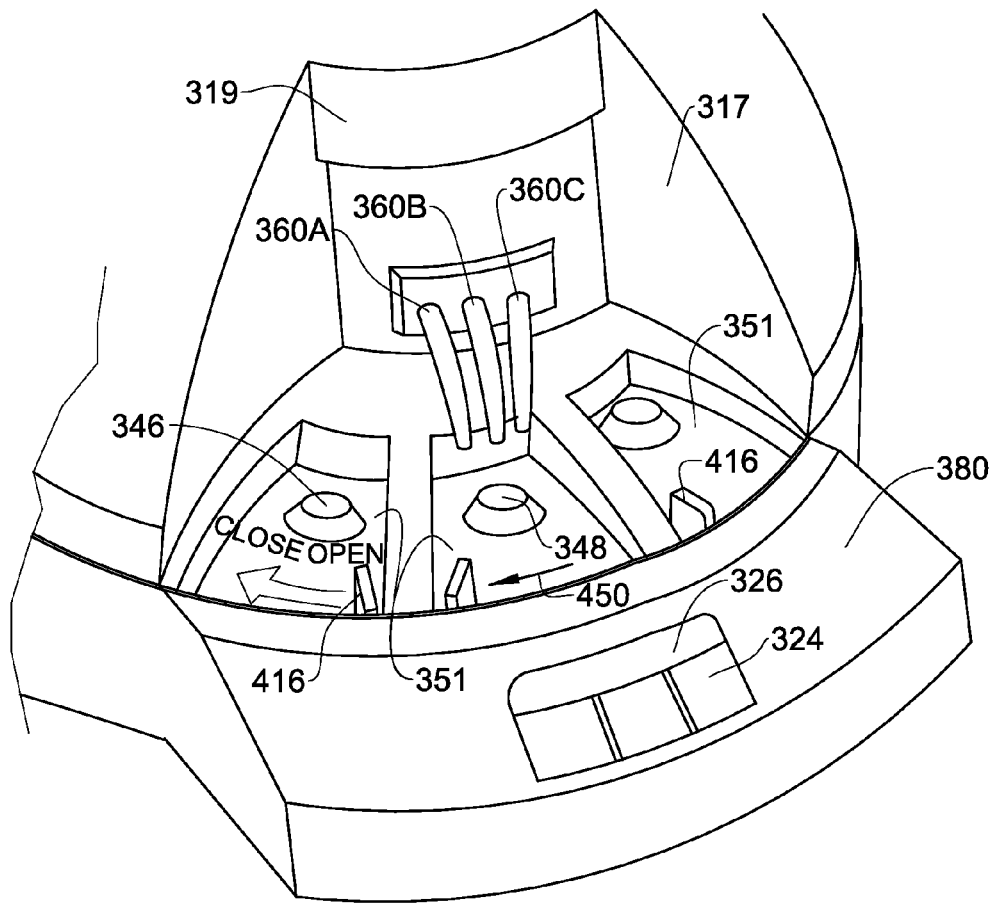
FIG. 14 is a schematic view of the dental restoration grip area of the device illustrated in FIG. 12.
Figure 15:
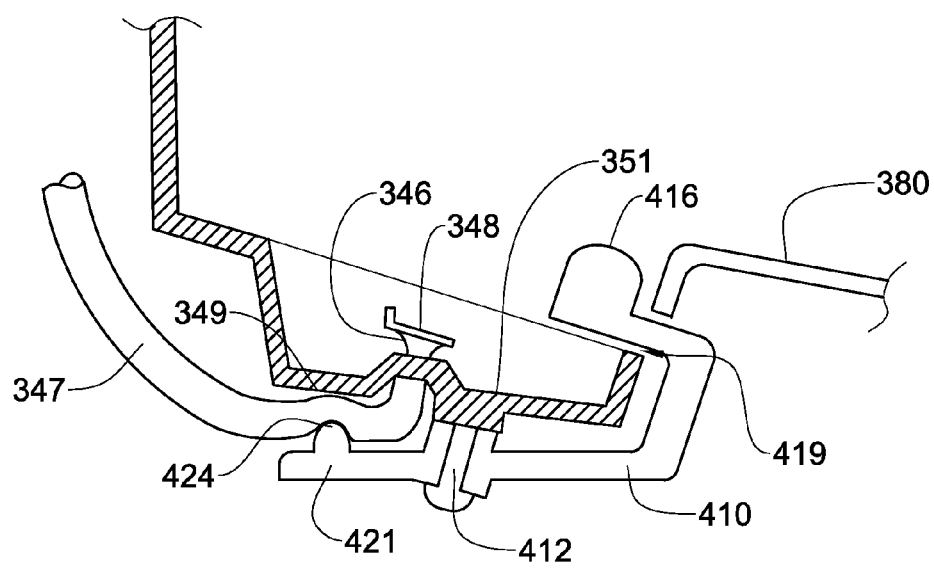
FIG. 15 is a section view of a dental restoration suction grip in accordance with the present invention.

Turning now to FIGS. 14 and 15, there is an illustration explaining how vacuum supply to the vacuum cups is provided or discontinued. Accordingly, each dental restoration grip is associated with a vacuum activated lever 410 pivotably secured to the base at 412 (FIG. 15) with a gripping portion 416 extending through slot 419. An end 421 of the lever 410 is formed with an upwardly extending projection 424 the arrangement being such that the lever 410 is pivotably displaceable between an open position (left most location in FIG. 14) wherein the projection 424 extends over the vacuum tube 347 pressing it against the rigid wall surface 349, thus discontinuing the vacuum towards the vacuum cup 346 wherein a dental restoration 348 may be easily placed or removed thereon. However, after applying the dental restoration 348 the lever 410 is displaced in direction of arrow 450 (FIG. 14) such that the projection 424 disengages from the vacuum tube 347 whereby suction now extends at the vacuum cup 346 to maintain the dental restoration at its position.

A sequence of operations performed on dental restoration within the apparatus in accordance with the present invention may include several steps performed at different stages and depending on the particular procedure carried out. Such operations will include, for example, cleaning a dental restoration (by applying thereon water or other cleaning agent), enhanced cleaning using ultrasonic vibrations, drying (by applying thereto air or warmed air), etching (e.g. by using a hydrofluoric acid), rinsing with fresh water, applying other agents such as an adhesive agent (Sailne), applying a bonding agent or different cements and so forth, flattening the applied layer/s by a fine jet of air, etc.

Figure 18:
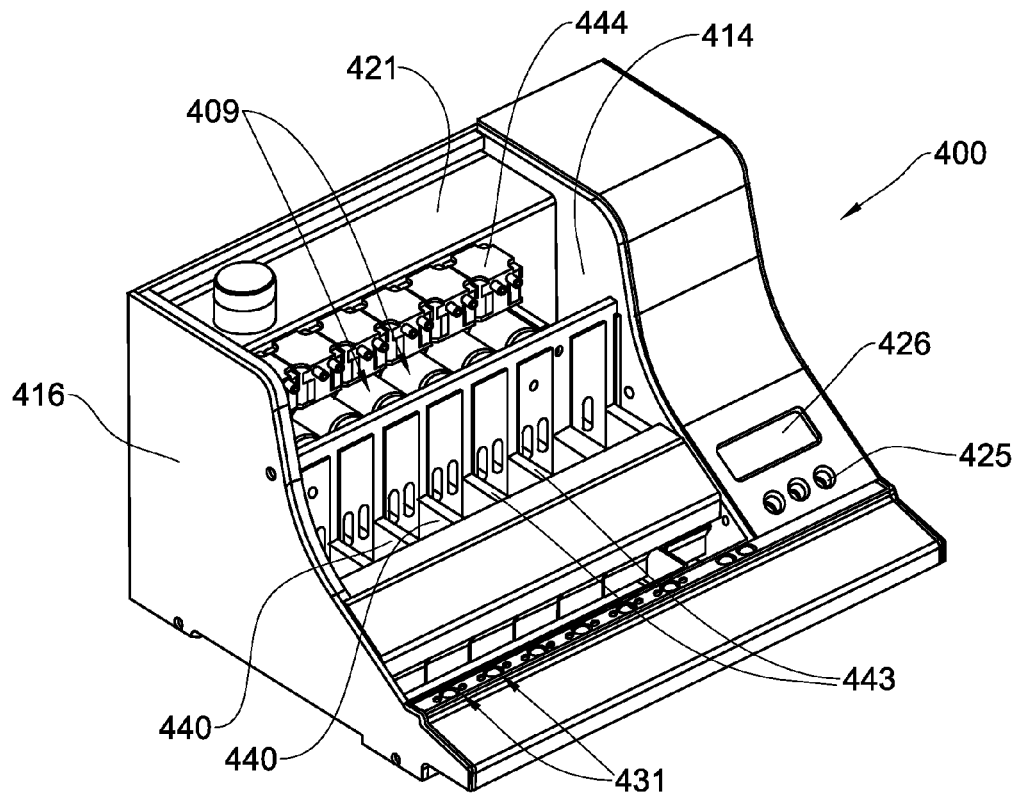
FIG. 18 is an isometric view of an apparatus according to another example of the present invention.
Figure 19:
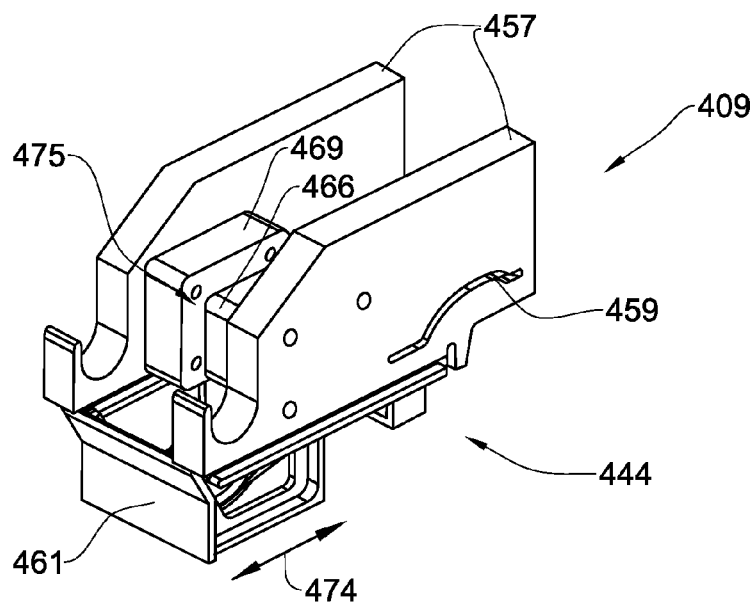
FIG. 19 is a front isometric view of a dental restoration grip assembly according to a particular example of the invention.

Further attention is now directed to FIG. 18 illustrating an apparatus generally designated 400, in accordance with a modification of the invention. The apparatus is a multiple-type dental restoration and conditioning apparatus, i.e. each dental restoration is separately treated, independent of neighboring units. For sake of clarity, lid 414 is made transparent for visualizing the sum of the internal components.

The housing 416 accommodates a large fluid reservoir 421 and comprises a plurality of confined dental restoration treating spaces 440 each extending between a pair of parallely extending walls 443, said walls extending substantially upright and together with a base portion (not seen) define a liquid internal basin (generally designated 451 and can best be seen in FIGS. 21 and 22), used for performing various procedures such as rinsing, ultrasonic treating of dental restorations, etc.

In the embodiment of FIG. 18 each confined space 440 is fitted with an independent dental restoration unit 409, each associated with an independent dental restoration grip unit generally designated 444 (best seen and discussed in detail with reference to FIGS. 21 and 22). Likewise, each confined space 440 is fitted with an applying nozzle (not seen) that is required for carrying out a procedure on the dental restoration, namely at least one fluid applying nozzles, sand-blasting, applying nozzle, and at least one drain outlet 447 for rinsing and draining each respective confined space 440.

Furthermore, since each of the treating spaces 440 is fitted with an individual dental restoration treating unit 409, thus, each such unit is associated with a central programmable controller of the apparatus 400 (of which a display panel 426 and touch sensor operating knobs 425 are seen, the programmable controller designed and programmed for carrying out a sequence of procedures as discussed hereinabove in connection with the previous embodiments.

As can further be seen, the housing 416 is fitted with an array of positions indicating LEDS 431 comprising a plurality of indicator LEDs 431, associated with each dental restoration unit 409 and being indicative of the relative operative state of the respective unit further providing indication regarding progress of the procedure carried out by the particular dental restoration unit 409, and other information such as, proper positioning of a dental restoration over the griping cups, etc.

Whilst each dental restoration unit 409 operates independent of neighboring such units, it is noticed that in order to minimize the overall footprint of the apparatus its weight and cost, several components are common for the unit, e.g. central controller, central waste container, common fluid containers (e.g. rinsing liquids, pressurized air, if not supplied by an external source), etc.

With further reference to FIGS. 19 to 22, there is illustrated a dental restoration unit 409 in accordance with the present invention. As mentioned hereinabove, each such unit is fitted within a dental restoration confined space 440 (FIG. 18) and is designed for operation and performing a sequence of treatments over a dental restoration, however independent of its neighboring restoration units 409.

Each unit 409 comprises a basing 451 (FIGS. 21A to 21C) defined between a pair of parallely extending, substantially upright walls 443, upwardly extending from a base 445, fitted with a drain port 447. The basing 451 is liquid impermeable and is suited for receiving therein different liquids, including those which may be abrasive.

Extending above the dental restoration unit 409 there is a dental restoration grip unit designated at 444 which as will be discussed hereinafter in further detail comprises a dental restoration grip mechanism displaceable between a loading/unloading position (FIGS. 21C and 22C), wherein the dental restoration (not shown) is loaded or unloaded on a respective grip, readily accessible upon opening of the lid 414 (FIG. 18). The unit is then displaceable into a treating position (FIGS. 21A and 22A) wherein the dental restoration grip, with a dental restoration thereon (not shown) is received within the basing 451, namely emerged within a liquid received therein, e.g. serving as an ultrasonic bath, etching bath or for any other treatment such as sand blasting and the like. At an intermediate position (FIGS. 21B and 22B) the dental restoration grip unit is partially retracted within the unit whereby other operations may be performed on a dental restoration such as blow drying, etc.

Each dental restoration grip unit 444 comprises a partition side wall 457 upwardly extending, substantially parallel to the side walls 443 of the basing 451, wherein said wall, apart from serving as a partition wall between neighboring dental restoration spaces 440 further serves as a guide for the dental restoration grip unit 409 and for that purpose it is formed with a curved cam-path 459, the arrangement being such that two neighboring walls 457 have their respective path 457 extending parallel to one another, i.e. facing one another.

The dental restoration grip unit 444 further comprises a grip carriage 461 formed with a pair of parallel side walls 463, each formed at its top edge with a tooth-rack 467 and a laterally extending shoulder 465 which is slideably receivable, in a reciprocal manner, within a slot 471 formed at the bottom end of partition wall 457. A power unit designated 478 comprises an electric motor unit 466 and a gear transmission 469 has two lateral cog wheels 472 (only one of which is seen in each of the respective drawings), and said power unit 478 is secured to the partition side wall 457 by means of holes extending through opening 471A (formed in the side wall 457) and 471B (formed in the power unit 478).

At the assembled position, the grip carriage 461 is received between the two neighboring partition walls 457 such that the gear 472 is engaged with the toothed rack 467, whereby rotation of the electric motor 466 generates rotary motion to the gears 472 resulting in axial reciprocal displacement of the grip carriage 461 (in a forward/backward direction as represented by arrowed line 474).

The dental restoration grip unit 444 further comprises a grip tray 475 formed at its rear end with a pair of laterally projecting pins 477 suited for sliding engagement within the cam-path slot 449, thus serving as a cam and follower couple, to be discussed hereinafter in further detail.

The grip tray 475 is pivotally secured to the grip carriage 461 by a pair of pivot pins 479 pivotally received within respective receptacle holes 481, whereby the grip tray 475 is capable of only pivotal rocking motion with respect to the grip carriage 461.

A replaceable dental restoration vacuum cup 491 is securely fitted over a support seat 496 (FIG. 20) formed at a front end of the grip tray 475, said dental restoration vacuum cup is coupled into a receptacle 498, and via a flexible tube 493 to a vacuum source (not seen). The arrangement is such that upon receipt of an appropriate signal the electric motor 466 it is initiated such that gears 472 rotate, resulting in forward/backward displacement of the grip carriage 461 with respect to the walls 457), resulting in turn in respective displacement of the grip tray 475 in a motion combined of forward/backward and pivotal displacement.

Figure 21A:
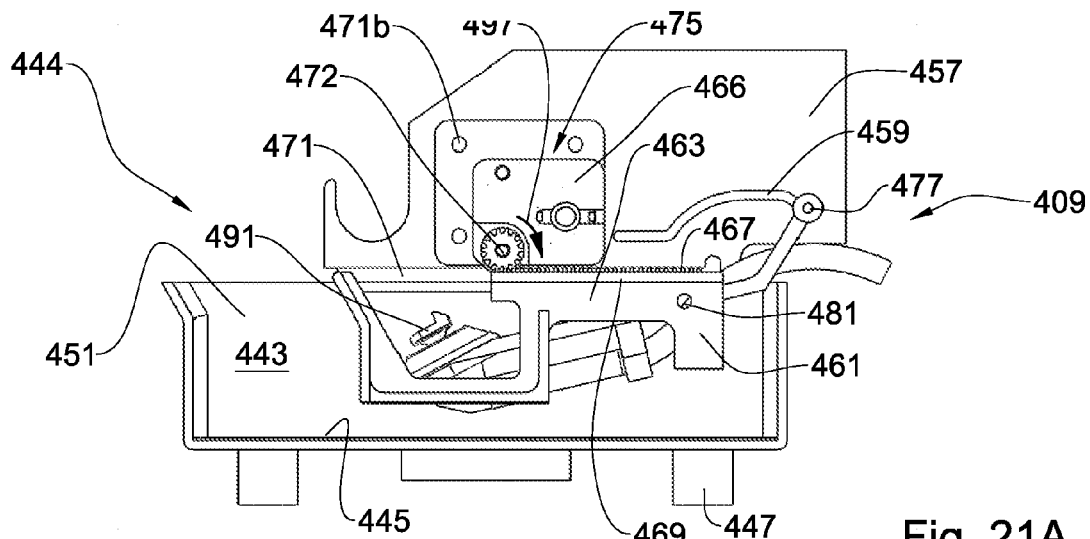
FIGS. 21A to 21C are side views of the dental restoration grip assembly of FIG. 19, illustrating consecutive steps of displacement thereof with respect to a fluid basin.
Figure 21B:
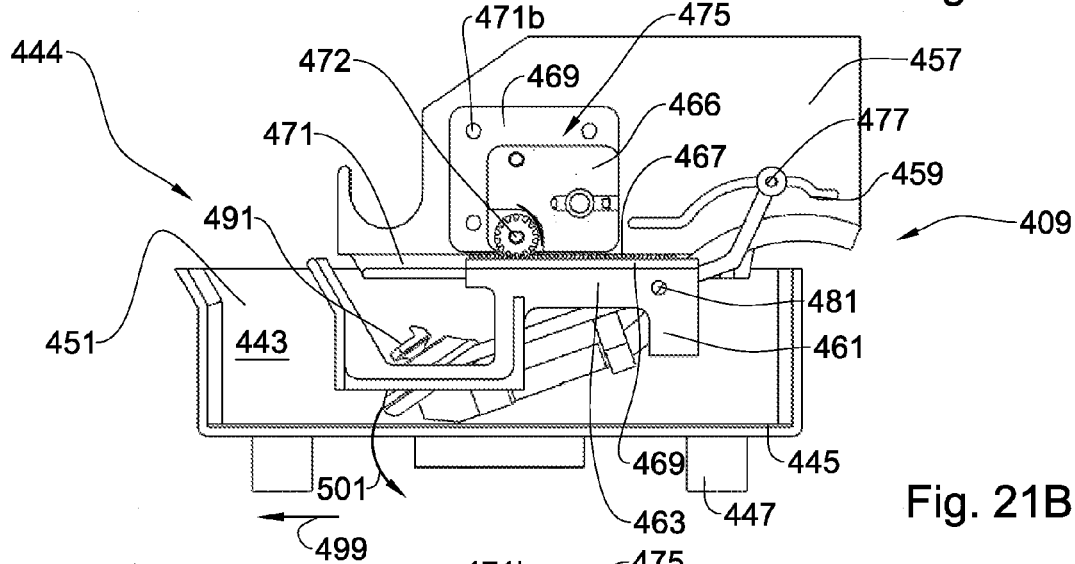
Figure 21C:
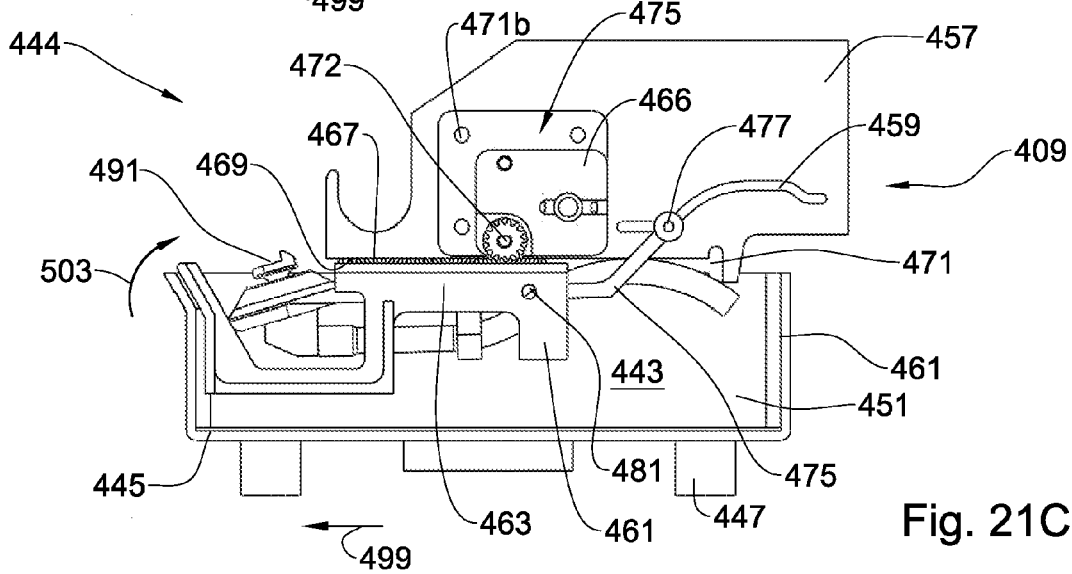
Figure 22A:
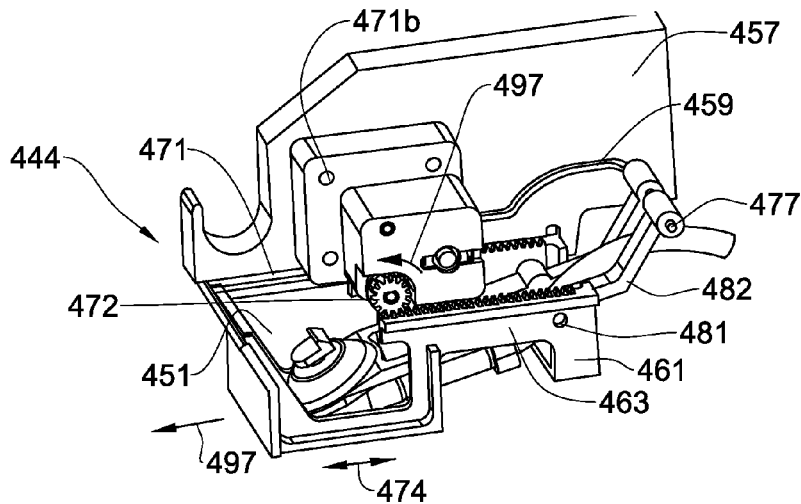
Figure 22B:
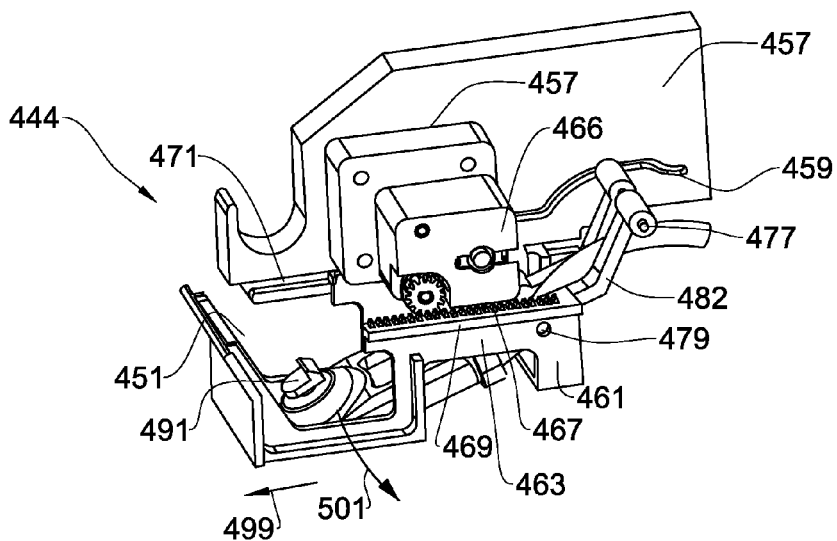
Figure 22C:
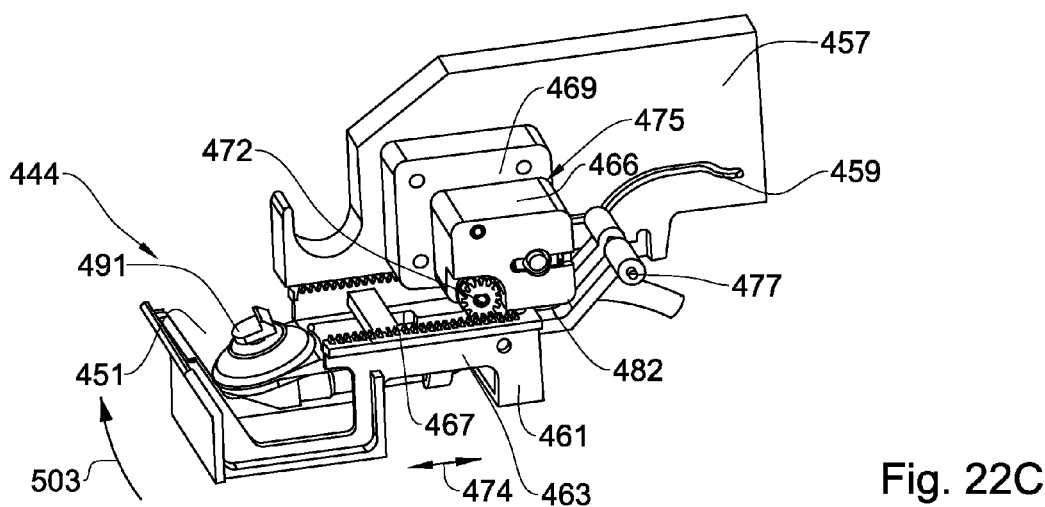

The position illustrated in respective FIGS. 21A and 22A illustrates the dental restoration unit 409 in an intermediate position, however received within the basing 451. Upon rotation of the gear wheels 472 in direction of arrow 497, the grip carriage 461 displaces forwards in direction of arrow 499 (FIGS. 21B and 22B), resulting in consequent forward displacement of the follower pins 477 within the cam path 459 which owing to the geometry of said path 459, the grip tray 475 pivots about pivot pins 479 in direction of arrow 501 (FIGS. 21B and 22B), whereby the vacuum cup 491 now expands at the lowermost position for treatment within the basing 451. Further rotation of the pinion gear 472, however in an opposite direction, entails forward displacement of the grip carriage 461 to its forward most position resulting, and consequent pivotal displacement of the grip tray 475 in direction of arrow 503, thus disposing the vacuum cup 491 in the so-called loading/unloading position wherein it emerges from the basing 451 such that a dental restoration may be applied/removed from the vacuum cup 491, ready for a new cycle.

Turning now to FIGS. 23A to 23H there are illustrated a variety of dental restoration vacuum cups fitted for cooperation with an apparatus in accordance with the present invention. Each of the FIGS. 23A to 23H provides a top perspective view and a respective longitudinal sectioned view, for understanding the structure of the vacuum cup.

The vacuum cups illustrated in FIGS. 23A to 23H are similar in their general construction however differ from one another in the fine and particular design of the suction element, as will be discussed hereinafter.

Figure 20:
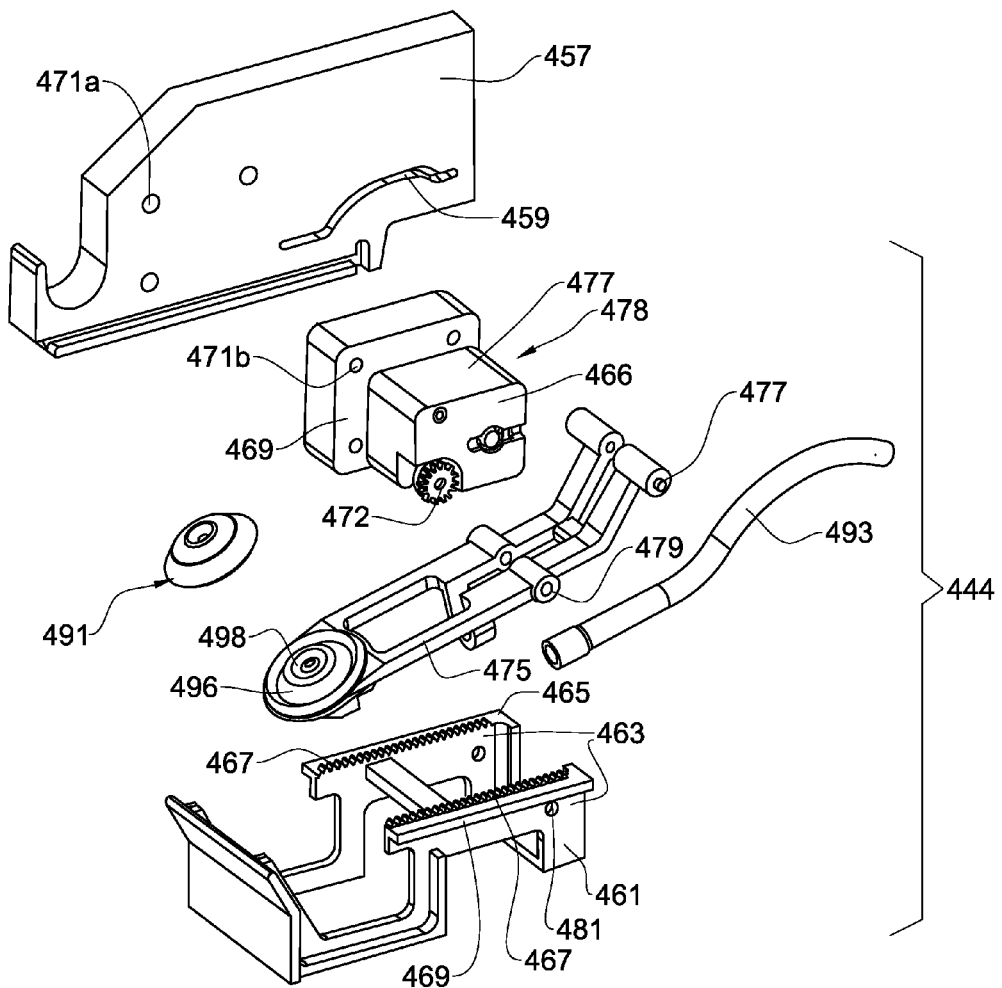
FIG. 20 is an isometric exploded view of the dental restoration grip assembly of FIG. 19.

Each of the suction units, typically made of silicone rubber or the like, comprises a tubular shank element 600 with an external wall 602 fitted for snuggly receiving within a receptacle 498 formed at a grip tray 475 (see for example FIG. 20), and further comprises a central bore 606 is provided for suction engagement over the vacuum supply pipe (493 in FIG. 20). The device comprises a support wall in the form of a skirt-like portion 610 such that when mounted on the grip tray 475 it firmly bears against a corresponding support surface (496 in FIG. 20). A resilient vacuum cup extends at an upper surface of each of the grips and is in flow communication with central bore 606 via a conduit 614. The vacuum cup in all of the embodiments has the general shape of an inverted dome and as already mentioned above, the differences between the examples of FIGS. 23A to 23H reside in the particular shape of the grip, as discussed hereinbelow.

In FIG. 23A the suction portion has a conical-cross section with walls tapering outwardly and having a substantial thick edge 620. In the embodiment of FIG. 23B, the suction portion has similar shape as in FIG. 23A however the walls are thinner and finer, with a fine lip 626. FIG. 23C illustrates a vacuum cup which has a crown-like shape with a bottom portion 630 resembling that disclosed in connection with FIG. 23B however with a fine annular lip 632 inwardly converging. The example of FIG. 23D illustrates a cup wherein the peripheral lip portion 636 is significantly finer than the base of the domed portion, said lip portion slightly diverging outwardly. FIG. 23E discloses an example which is similar to that disclosed in FIG. 23D however with a thicker lip 640. FIG. 23F illustrates an example in which thickness of the wall of the domed portion converges outwardly and further the general structure of the wall is thinner as compared with previous embodiments. FIG. 23G illustrates an embodiment wherein the lip 648 converges outwardly and has a downwardly projecting portion 650 whereby in fact the edges of the lip do not engage a dental restoration when applied thereon. FIG. 23H differs from the previous embodiments in that the domed-cup is substantially concave however slightly oval rather than circular, and having fine lips.

In the examples of FIGS. 23A to 23G the dental restoration grips are formed with a skirt-like wall portion 610 for protection concealment of a holder thereof. This is in particular useful when sand blasting is to be applied to the restoration grip and thus the skirt-like portion protects the grip holder from wear during the sand blasting procedure.

However, the example of FIG. 23H illustrates a dental restoration grip formed without said skirt portion, namely formed with a substantially tubular coupling neck which may be coupleable in different forms to a vacuum source.

It is appreciated that whilst several particular examples of vacuum cups have been illustrated, a person versed in the art may combine any of these shapes or introduce further shapes which fall within the scope of the general concept.

Figure 24A:
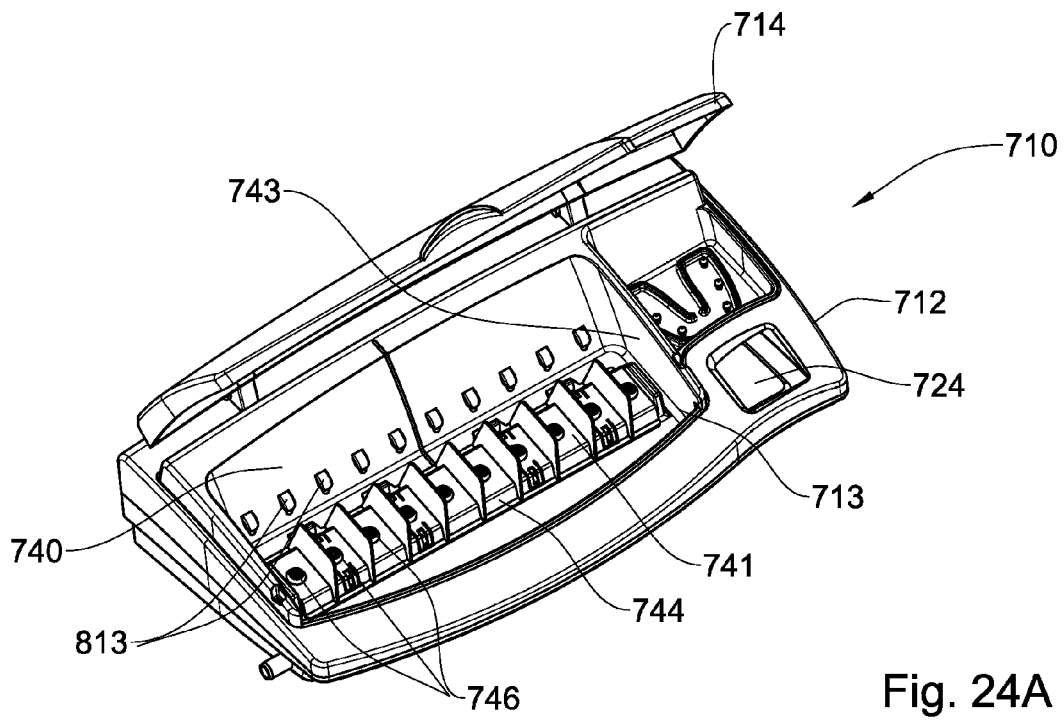
FIG. 24A is an isometric view of still another embodiment of the apparatus according to the present invention with the lid at its open position.
Figure 24B:
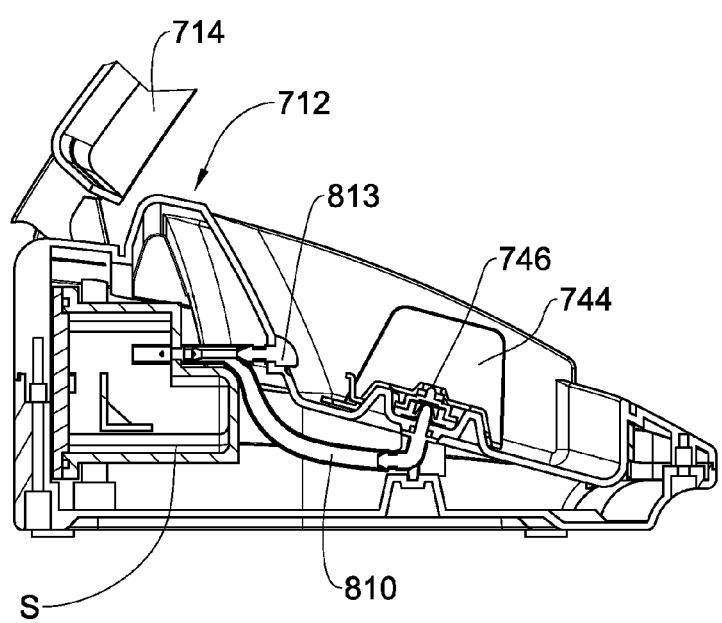
FIG. 24B is a sectioned side view of a portion of the apparatus of FIG. 24A, illustrating the connection of the vacuum cups to the vacuum source.

With reference to FIGS. 24A and 24B, there is illustrated another configuration of the dental restoration conditioning apparatus in accordance to the presently disclosed subject matter. The apparatus now generally designated 710 comprises some of the elements substantially similar at least to the embodiment described with respect to FIGS. 1 and 2, designated with the same reference numerals however shifted by 700.

The apparatus 710 comprises a housing 712 sized suitably for being a desk top a) device, fitted with a basin 713 and possibly fitted with a lid 714 pivotable with respect to the housing between a closed position (not shown) and an open position (FIGS. 24A and 24B).

The lid 714 together with the housing 712, and specifically the basin 713, define a fluid tight dental restoration treating space 740 fitted with a dental restoration grip generally designated 744 and comprising an array of vacuum cups 746 each suited for vacuum gripping of a dental restoration (not shown).

The lid 714 is made translucent, or may have only a transparent window portion allowing visualizing the dental restoration grip 744.

Figure 25A:
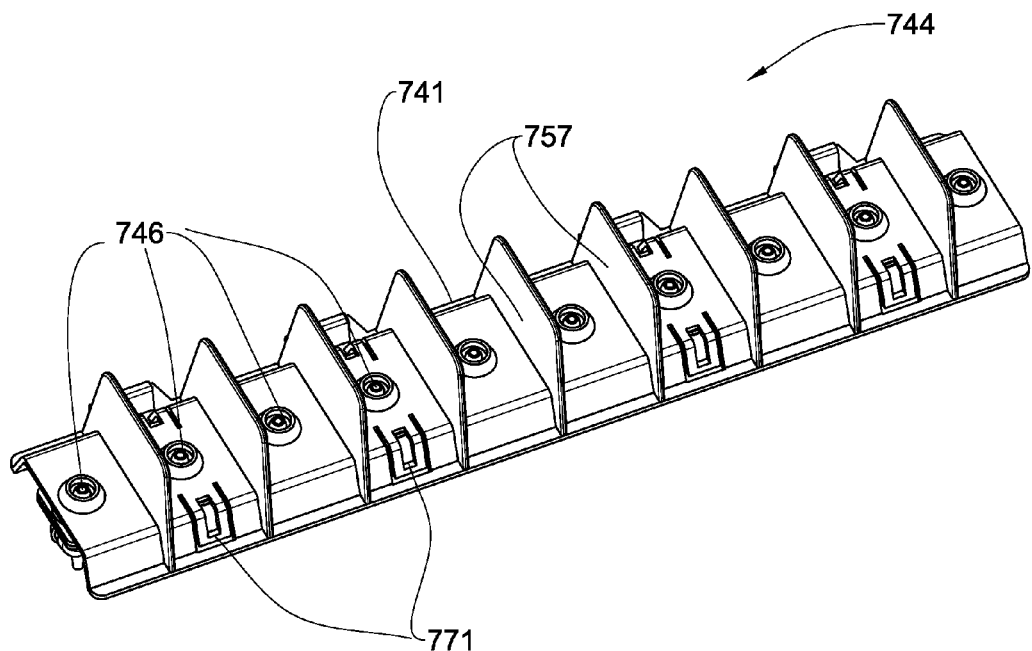
FIG. 25A is an isometric view of the disposable grip of the apparatus of FIGS. 24A and 24B.
Figure 25B:
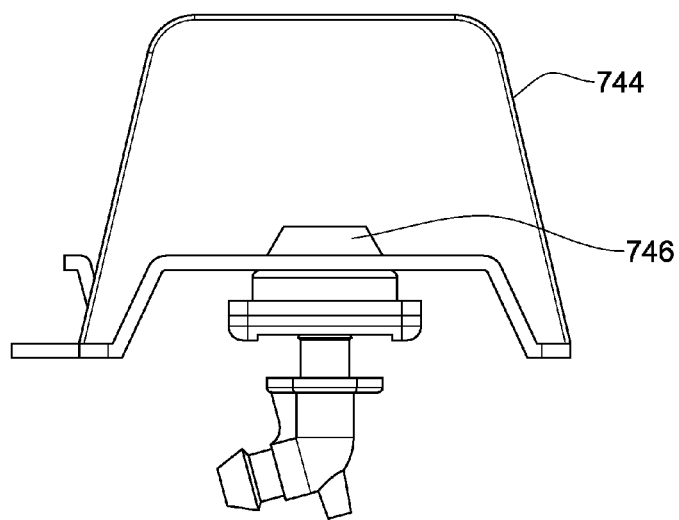
FIG. 25B, is a side view of a section of the grip of FIG. 25A, together with the vacuum cup.

The grip 744 shown in FIGS. 25A and 25B, is a disposable member and can be easily removed from the housing 712 and replaced when necessary. In accordance with one embodiment the disposable grip 744 is a uniform array fitted with a plurality of the vacuum cups 746. In such a case, the grip 744 is configured to be replaced together with the cups 746. The replacement may take place between different sequences of the same procedure and/or between different procedures.

The grip 744 comprises partition side walls 757 upwardly extending, substantially parallel to the side walls 743 (FIG. 24A) of the basin 713, serving as partition walls between neighboring dental restoration spaces 741 to thereby prevent, for example, splashing of agent therebetween.

The grip 744 further comprises grasps 771 for detachably attaching the grip 744 within the housing 712.

In accordance with another embodiment of the presently disclosed subject matter (not shown) the grip may be constituted of independent disposable resilient vacuum cups, each associated with its own independent grip and each configured to be independently replaced.

In both above embodiments, the cups are designed to suit different sizes of dental restorations as well as different shapes thereof (e.g. making rendering it suitable for use in conjunction with veneers, crowns, inlays, onlays, bridges and the like). A variety of dental restoration vacuum cups fitted for cooperation with an apparatus in accordance with the present invention are illustrated in FIGS. 23A to 23H and described above.

The apparatus 710 further comprises a programmable controller 724 (FIG. 24A), which, according to this embodiment is a timer, for governing the procedures performed by the apparatus 710. The controller 724 may be programmed to automatically carry out a sequence of operations, though it may be manually interrupted at any time with an internal clock governing the procedures which often require precise timing.

The controller 724 may be controllable via a control panel, via a display panel and/or a plurality of panel operating knobs (all not shown).

The apparatus 710 further comprises a drain for withdrawal of any waste liquid and debris generated during performing of the procedures. The drain may be in a form of a drain port or a waste container for maintaining the waste drain liquid therewithin.

Figure 26:
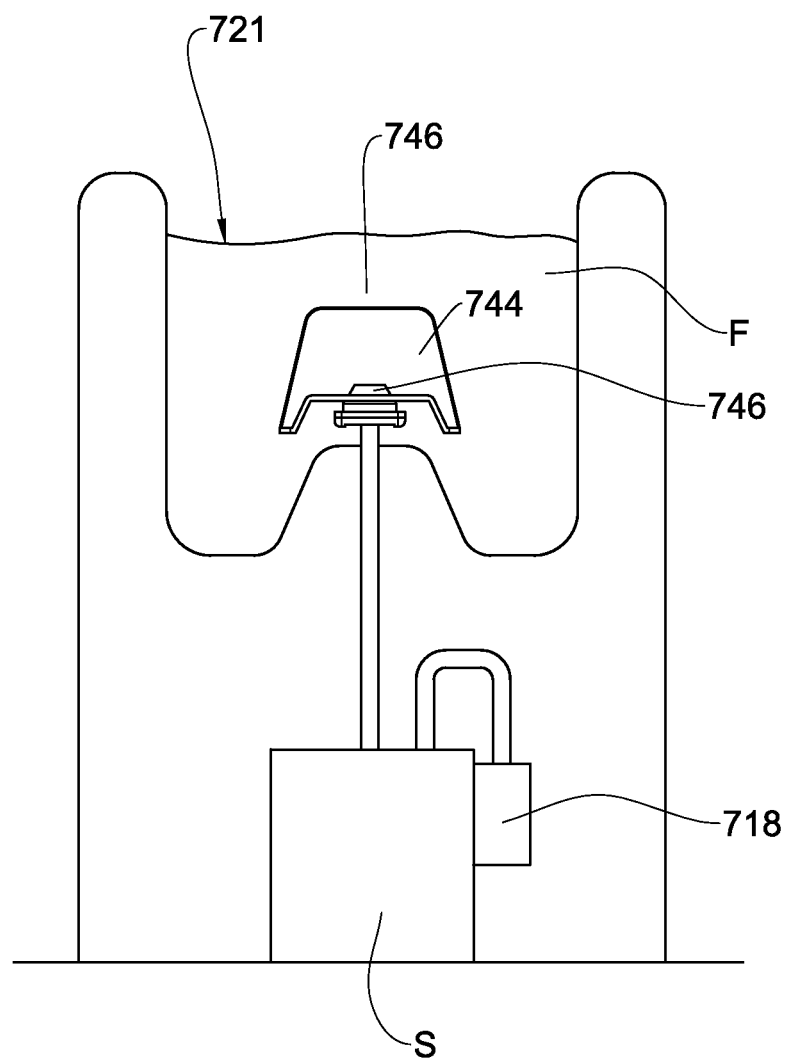
FIG. 26 is a schematic illustration of another embodiment of the apparatus according to the present invention.

With reference to FIG. 26, the basin of the housing may be formed as a large fluid reservoir 721 extending along both sides of the grip 744. Normally, the reservoir 721 is in fluid communication with a drain channel 718. However, the drain channel 718 may be sealed, to allow the filling of the reservoir 721 with fluid F above the cup 746 for performing various procedures such as rinsing, ultrasonic treating of dental restorations, etc.

Reverting now to FIG. 25B, there is shown how vacuum supply to the vacuum cups is provided. According to this specific embodiment, each vacuum cup is in flow communication with its corresponding vacuum source S through a connection pipe 810. Alternatively, vacuum cups may be divided to groups, each group connected to one vacuum source, or all the cups may be connected to a single vacuum source.

The apparatus further comprises air exhausts 813 all being in flow communication with a common air outlet port (not shown) and, possibly with the drain port.

It should be appreciated that the apparatus according to FIGS. 24 to 26, as described above, may comprise at least one of the features described with reference to the embodiments illustrated in the preceding figures.

Those skilled in the art to which this invention pertains will readily appreciate that numerous changes, variations, and modifications can be made without departing from the scope of the invention, Mutatis Mutandis.

The invention claimed is:

1. A dental restoration conditioning apparatus comprising, a housing formed with a liquid-tight dental restoration treating space comprising a liquid drain, said housing configured with a disposable dental restoration grip comprising at least one resilient vacuum cup, each of said at least one resilient vacuum cup being in fluid communication with at least one vacuum source; and at least one fluid applying nozzle,
wherein at least one of said at least one resilient vacuum cup and at least one fluid applying nozzle is displaceable with respect to another of said at least one resilient vacuum cup and at least one fluid applying nozzle, and a supply of at least one fluid agent being in fluid communication with said fluid applying nozzle.

2. The apparatus according to claim 1, wherein said disposable grip is a uniform array fitted with said at least one resilient vacuum cup.

3. The apparatus according to claim 1, wherein said disposable grip is constituted of a plurality of disposable individual grips each fitted with a resilient vacuum cup.

4. The apparatus according to claim 1, wherein each of said at least one resilient vacuum cup is in fluid communication with their corresponding at least one vacuum source.

5. The apparatus according to claim 1, wherein said at least one resilient vacuum cup is connected to a single vacuum source.

6. The apparatus according to claim 1, wherein the housing is fitted with a plurality of treating spaces, each fitted with a resilient vacuum cup and at least one fluid applying nozzle, each treating space is configured for performing an independent sequence of operations on a dental restoration received therein.

7. The apparatus according to claim 1, wherein the fluid applying nozzle is displaceable so as to cooperate with each location of said at least one resilient vacuum cup.

8. The apparatus according to claim 1, wherein said at least one resilient vacuum cup is disposed on a carousel-like tray, and one or two of the at least one resilient vacuum cup and the at least one fluid applying nozzle are rotatable with respect to one another.

9. The apparatus according to claim 1, wherein the supply of at least one fluid agent comprises at least one of fresh water supply, air supply and surface treating agent supply.

10. The apparatus according to claim 1, further comprising a programmable controller.

11. The apparatus according to claim 1, wherein the liquid drain is in fluid communication with a disposable waste container articulated with the apparatus.

12. The apparatus according to claim 1, wherein the treating space is fitted with a protective door, said door formed with at least a visor portion for visualizing said treating space.

13. The apparatus according to claim 1, further comprising an internal illumination source.

14. The apparatus according to claim 1, further comprising a light source for selective and controllable light curing.

15. The apparatus according to claim 1, wherein the at least one resilient vacuum cup is replaceable so as to conform with various shapes and sizes of dental restorations.

16. The apparatus according to claim 1, wherein during a conditioning process partitionings are provided between neighboring vacuum cups, to thereby prevent splashing of agent therebetween.

17. The apparatus according to claim 1, wherein the dental restoration grip is fitted with a vacuum actuating mechanism whereby vacuum is applied only upon presenting a dental restoration over a respective vacuum cup.

18. A method for conditioning a surface of a dental restoration, comprising:
  obtaining a dental restoration conditioning apparatus comprising a housing formed with a liquid-tight dental restoration treating space comprising a liquid drain, said housing configured with a disposable dental restoration grip comprising at least one resilient vacuum cup, each of said at least one resilient vacuum cup being in fluid communication with at least one vacuum source, at least one fluid applying nozzle, and a programmable controller, wherein at least one of said at least one resilient vacuum cup and at least one fluid applying nozzle is displaceable with respect to another of said at least one resilient vacuum cup and at least one fluid applying nozzle, and a supply of at least one fluid agent being in fluid communication with said fluid applying nozzle;
  securely applying a dental restoration on the resilient vacuum cup;
  activating the controller to generate control signals for a conditioning process; and
  removing the dental restoration.

19. A dental restoration conditioning apparatus comprising a housing formed with a liquid tight dental restoration treating space, said housing fitted with a dental restoration grip comprising at least one resilient vacuum cup configured for securely applying a dental restoration thereon, at least one fluid applying nozzle, wherein at least one of said at least one resilient vacuum cup and at least one fluid applying nozzle is displaceable with respect to another of said at least one resilient vacuum cup and at least one fluid applying nozzle; a supply of at least one fluid agent being in fluid communication with said fluid applying nozzle, a fluid drain from said treating space, and a programmable controller.

20. A method for conditioning a surface of a dental restoration, comprising:
  obtaining a dental restoration conditioning apparatus comprising a housing formed with at least one liquid tight dental restoration treating space, said housing fitted with a dental restoration grip comprising at least one resilient vacuum cup, at least one fluid applying nozzle, wherein at least one of said at least one resilient vacuum cup and at least one fluid applying nozzle is displaceable with respect to another of said at least one resilient vacuum cup and at least one fluid applying nozzle; a supply of at least one fluid agent being in fluid communication with said fluid applying nozzle, a fluid drain from said treating space, and a programmable controller;
  securely applying a dental restoration on the resilient vacuum cup;
  activating the controller to generate control signals for a conditioning process; and
  removing the dental restoration.

21. A dental restoration conditioning apparatus, comprising, a housing formed with a liquid-tight dental restoration treating space comprising a liquid drain, said housing configured with a disposable dental restoration grip comprising at least one resilient vacuum cup configured for easy replacement to suit different sizes of dental restorations as well as different shapes thereof, and for fitting over a substantially rigid grip seat coupled to a suction line, each of said at least one resilient vacuum cup being in fluid communication with at least one vacuum source; and
  at least one fluid applying nozzle,
  wherein at least one of said at least one resilient vacuum cup and at least one fluid applying nozzle is displaceable with respect to another of said at least one resilient vacuum cup and at least one fluid applying nozzle, and a supply of at least one fluid agent being in fluid communication with said fluid applying nozzle.

22. A method for conditioning a surface of a dental restoration, comprising:
  obtaining a dental restoration conditioning apparatus comprising a housing formed with a liquid-tight dental restoration treating space comprising a liquid drain, said housing configured with a disposable dental restoration grip comprising at least one replaceable and/or disposable resilient vacuum cup configured for easy replacement to suit different sizes of dental restorations as well as different shapes thereof, and for fitting over a substantially rigid grip seat coupled to a suction line, each of said at least one resilient vacuum cup being in fluid communication with at least one vacuum source, at least one fluid applying nozzle, and a programmable controller, wherein at least one of said at least one resilient vacuum cup and at least one fluid applying nozzle is displaceable with respect to another of said at least one resilient vacuum cup and at least one fluid applying nozzle, and a supply of at least one fluid agent being in fluid communication with said fluid applying nozzle;

securely applying a dental restoration on the resilient vacuum cup;

activating the controller to generate control signals for a conditioning process; and removing the dental restoration.

23. A dental restoration conditioning apparatus comprising a housing formed with a liquid tight dental restoration treating space, said housing fitted with a dental restoration grip comprising at least one replaceable resilient vacuum cup configured for easy replacement to suit different sizes of dental restorations as well as different shapes thereof, and for fitting over a substantially rigid grip seat coupled to a suction line, at least one fluid applying nozzle, wherein at least one of said at least one resilient vacuum cup and at least one fluid applying nozzle is displaceable with respect to another of said at least one resilient vacuum cup and at least one fluid applying nozzle; a supply of at least one fluid agent being in fluid communication with said fluid applying nozzle, a fluid drain from said treating space, and a programmable controller.

24. A method for conditioning a surface of a dental restoration, comprising:

obtaining a dental restoration conditioning apparatus comprising a housing formed with at least one liquid tight dental restoration treating space, said housing fitted with a dental restoration grip comprising at least one replaceable resilient vacuum cup configured for easy replacement to suit different sizes of dental restorations as well as different shapes thereof, and for fitting over a substantially rigid grip seat coupled to a suction line, at least one fluid applying nozzle, wherein at least one of said at least one resilient vacuum cup and at least one fluid applying nozzle is displaceable with respect to another of said at least one resilient vacuum cup and at least one fluid applying nozzle, a supply of at least one fluid agent being in fluid communication with said fluid applying nozzle, a fluid drain from said treating space, and a programmable controller;

securely applying a dental restoration on the resilient vacuum cup;

activating the controller to generate control signals for a conditioning process; and removing the dental restoration.

\* \* \* \* \*